United States Patent [19]
Watson, Jr. et al.

[11] Patent Number: 5,788,715
[45] Date of Patent: Aug. 4, 1998

[54] TELESCOPING SERIAL ELASTIC BAND LIGATOR

[75] Inventors: Thomas E. Watson, Jr., Hooksett, N.H.; Harold Mark Aznoian, North Andover, Mass.; Ronald B. Lamport, Pelham, N.H.; Paul D. Gillette, Lowell, Mass.; Donald Golden, Cherry Hill, N.J.; Nasser Rafiee, Andover, Mass.

[73] Assignee: C.R. Bard, Inc., Murray Hill, N.J.

[21] Appl. No.: 727,489
[22] PCT Filed: Feb. 7, 1995
[86] PCT No.: PCT/US95/01611
§ 371 Date: May 8, 1997
§ 102(e) Date: May 8, 1997
[87] PCT Pub. No.: WO96/24292
PCT Pub. Date: Aug. 15, 1996
[51] Int. Cl.⁶ ............................................. A61B 17/04
[52] U.S. Cl. ............................................. 606/140; 606/141
[58] Field of Search ................................. 606/139, 140, 606/141, 144

[56] References Cited

U.S. PATENT DOCUMENTS

| | | | |
|---|---|---|---|
| 1,625,602 | 4/1927 | Gould et al. | |
| 3,760,810 | 9/1973 | Van Hoorn | 128/326 |
| 3,985,138 | 10/1976 | Jarvik | 128/326 |
| 4,226,239 | 10/1980 | Polk et al. | 128/303 |
| 4,735,194 | 4/1988 | Stiegmann | 128/6 |
| 4,860,746 | 8/1989 | Yoon | 128/326 |
| 5,207,690 | 5/1993 | Rohrabacher et al. | 606/135 |
| 5,269,789 | 12/1993 | Chin et al. | 606/140 |
| 5,356,416 | 10/1994 | Chu et al. | 606/140 |

Primary Examiner—Gary Jackson
Attorney, Agent, or Firm—Darby & Darby

[57] ABSTRACT

A ligating band dispenser has a plurality of elastic ligating bands at least one of which is supported on each of a series of partially nested cylinders. Inner and intermediate cylinders comprise axially sliding cylinders for dispensing the ligating bands. An outer cylinder, which may be attached to the distal end of an elongated introducer, surrounds at least the proximal portion of the intermediate cylinder and is adapted to receive the sliding cylinders slide into its distal end. A trip wire is connected to the inner cylinder and extends proximally therefrom through the elongated introducer. The trip wire is adapted to cause an axially sliding motion of the sliding cylinders during an application of force to the trip wire. A restraining means is associated with each sliding cylinder to restrain sliding motion thereof during the application of force to the trip wire. Finally, a releasing means is provided to release the restraining means associated with one of the sliding cylinders upon the application of the pulling force. The released sliding cylinder slides in response to the applied pulling force while a distal end of one of the intermediate and outer cylinders pushes the ligating band therefrom. According to this construction, at least two ligating bands may be independently dispensed onto tissue at one or more designated sites thereby accomplishing ligation thereof.

51 Claims, 9 Drawing Sheets

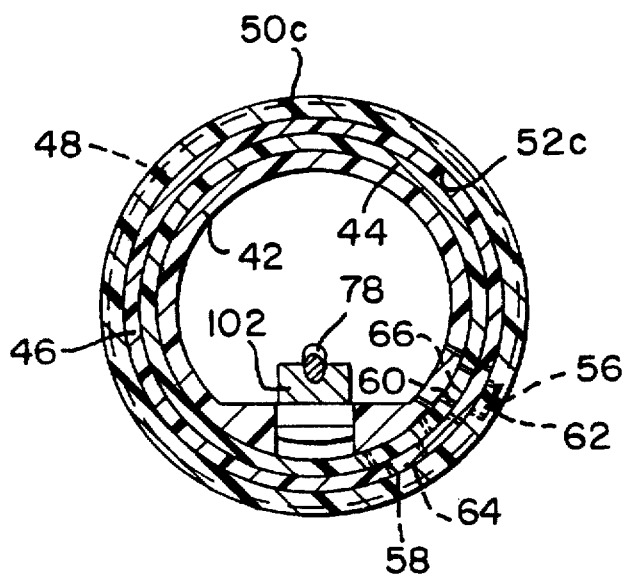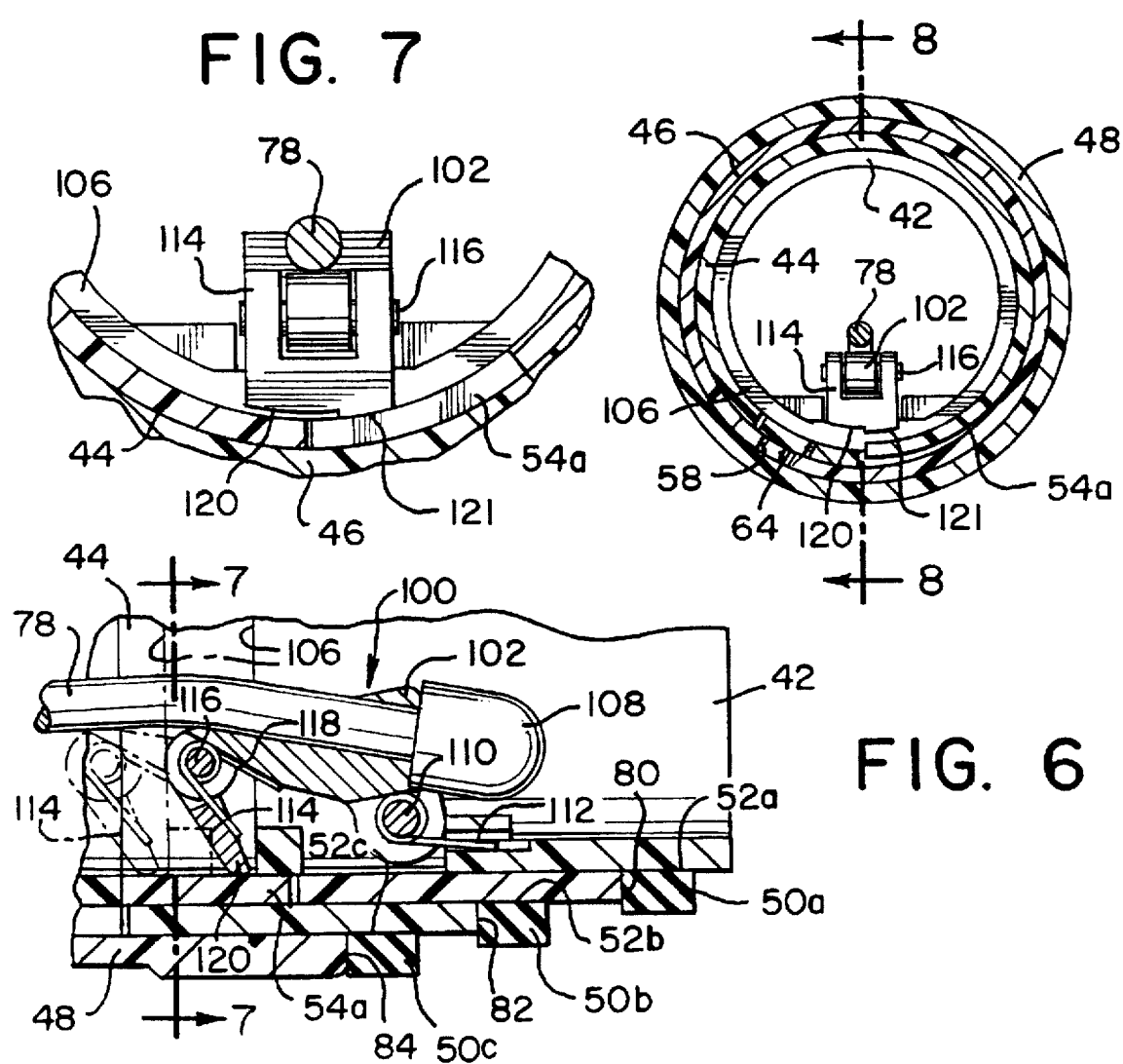

FIG. 13
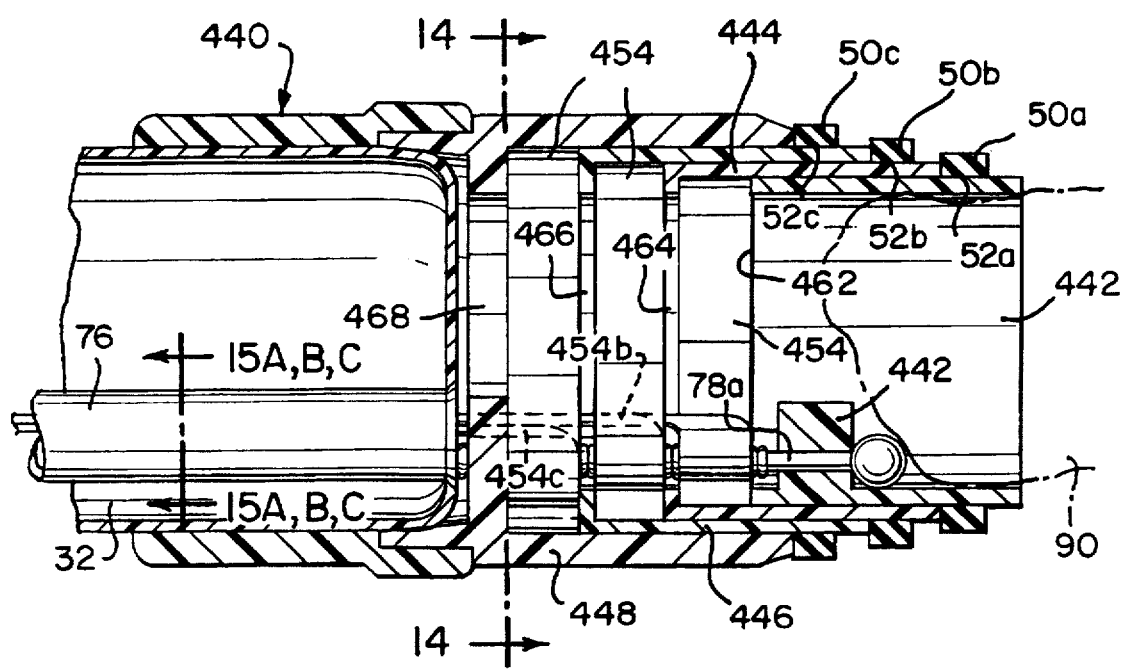
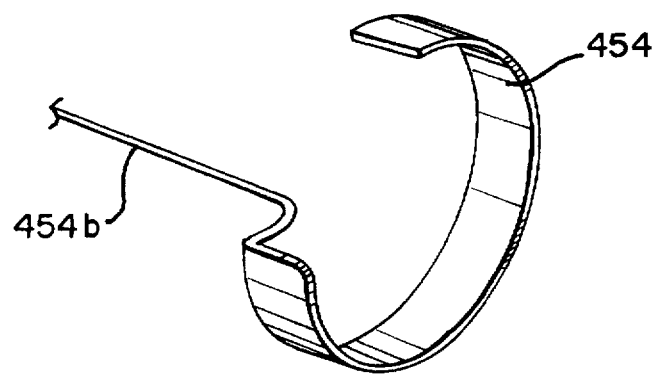
FIG. 13A

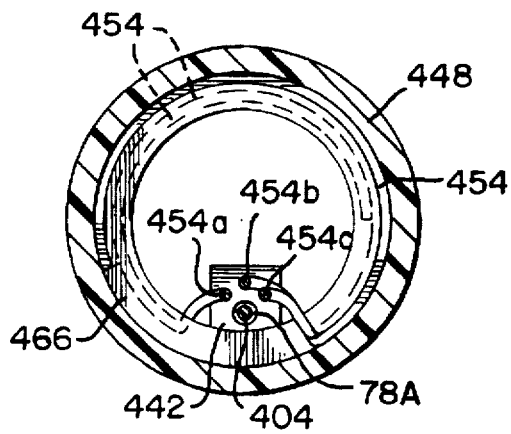
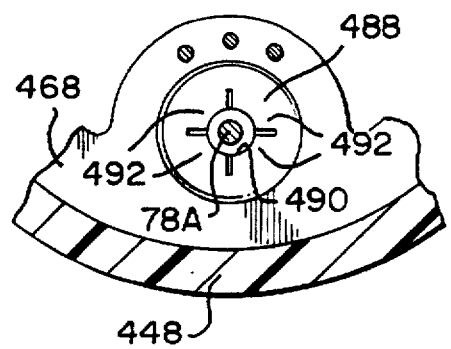
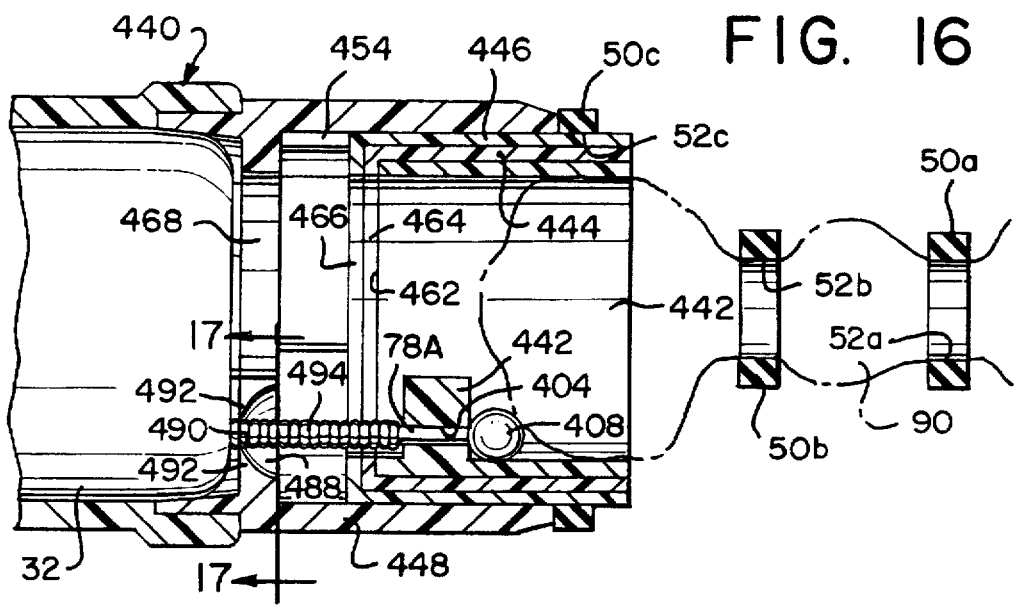

TELESCOPING SERIAL ELASTIC BAND LIGATOR

BACKGROUND OF THE INVENTION

1. Field of the Invention

This invention generally relates to ligating instruments and more particularly to instruments for dispensing a plurality of ligating bands to one or more internal sites within a patient's body in a single ligation procedure, without removing the instrument between successive ligating band placements.

2. Brief Description of Related Art

The treatment of various types of lesions including internal hemorrhoids by ligation is well known. The object of ligation is to position an elastic cord, or ligating band, at the lesion to stop circulation through tissue and allow the tissue to necrose whereupon the body sloughs off the necrotic or dead tissue.

Surgical ligation has also been employed in female and male sterilization procedures. In the case of tubal ligation in female patients, ligating rings or bands are placed on a folded-over loop portion of each Fallopian tube, blocking the path from uterus to ovaries, and thereby preventing fertilization of an ovum. In the case of male sterilization, a ligating band may similarly be placed on a folded-over loop portion of the vas deferens, thus preventing passage of spermatozoa from the testes.

The following United States Letters Patent disclose various embodiments of ligating instruments: U.S. Pat Nos. 3,760,810 to Van Hoorn; 4,257,419 to Goltner, et al.; and 4,735,194 to Stiegmann.

U.S. Pat. No. 3,760,810 to Van Hoorn discloses an instrument for facilitating the placement of a single ligating band or set of bands. The instrument includes, at its distal end, a ligating band dispenser comprising two rigid, concentric tubes. The tubes can slide with respect to each other under the control of a trigger mechanism at the proximal end of the instrument. A rigid endoscope having internal passages forming a suction path and a light path interconnect the trigger mechanism and dispenser. The inner tube can be loaded with a set of one or more elastic rings or ligating bands. A separate stopper bar attaches to the instrument to prevent premature dispensing. When the instrument is located proximate to a lesion, a surgeon removes the stopper bar and applies vacuum to draw tissue into a hollow passage at the distal end of the instrument. Pulling on the trigger retracts the inner tube. A radial surface or shoulder on the outer tube engages the ligating band so it can not displace with the inner tube. As the inner tube is withdrawn from the ligating band, it collapses onto the tissue.

U.S. Pat. No. 4,257,419 to Goltner, et al. discloses a rigid endoscope that includes a ligating band dispenser with an inner tube that moves with respect to an outer tube to dispense a ligating band. This dispenser is oriented at right angles to the rigid endoscope and includes a structure for moving the inner tube of the dispenser in this configuration.

U.S. Pat. No. 4,735,194 to Stiegmann discloses a flexible endoscope ligating instrument in which a flexible endoscope structure includes a biopsy channel and a suction channel extending between the proximal and distal ends. A dispenser, like the dispenser structure shown in the Van Hoorn and Goltner patents, includes an inner tube that moves axially with respect to an outer tube at the distal end of the instrument. The outer tube connects to the distal end of the endoscope. An operating mechanism in the form of a pull wire with a weighted handle maintains tension on the inner tube so it does not displace axially outward while the instrument is being positioned. For some applications it is suggested that the endoscope structure be inserted through an overtube to prevent premature dispensing. Suction can be applied to draw tissue into a central aperture of the dispenser. Then a surgeon pulls the handle and retracts the inner tube axially past the distal end of the outer tube to force the ligating band off the instrument onto the tissue.

Each of the foregoing instruments dispenses a single ligating band or a single set of ligating bands at a single location. None of the patents suggests dispensing ligating bands at discrete locations. The Van Hoorn patent does disclose the possibility of depositing plural ligating bands. However, Van Hoorn seems only to suggest dispensing plural ligating bands at a single site in a single operation. The apparatus disclosed in the Van Hoorn, Goltner or Stiegmann patents apparently would have to rely on a surgeon's sense of touch in order to displace the inner tube by an incremental distance corresponding to the thickness of a stretched ligating band to deposit a plurality of bands at different sites. That would be very difficult to accomplish.

With the foregoing described devices, when it is desired to deposit ligating bands at different sites, the common practice was to withdraw the entire instrument from the patient and load a new ligating band onto the inner tube. Loading ligating bands on an instrument requires special tools and could be time consuming particularly if the special tooling must be retrieved to install each ligating band individually while the instrument is withdrawn. Each of these instruments requires some structure, such as special stoppers or overtubes, for preventing the premature dispensing of the ligating band. Consequently, none of these instruments was readily adapted for dispensing ligating bands at different sites without withdrawing the instrument after each individual site is ligated.

Aimed at solving the aforementioned problems, the following United States Letters Patent disclose various embodiments of ligating instruments which are designed to deposit or place a plurality of ligating bands at one or more internal sites within a patient without the necessity of withdrawing the ligating instrument to reload successive ligating bands: U.S. Pat. Nos. 3,985,138 to Jarvik; 4,226,239 to Polk et al.; 3,870,048 to Yoon; 5,207,690 to Rohrabacher et al.; and 5,269,789 to Chin.

U.S. Pat. No. 3,985,138 to Jarvik discloses a ligature gun for placing a plurality of preformed suture loops which are tightened around bleeders after emplacement. The successive preformed suture loops are advanced to the dispensing end of the ligature gun by rotation of a threaded rod onto which the loops have been preloaded. The Jarvik ligature gun comprises large number of mechanical parts and is relatively complex in design and operation.

U.S. Pat. No. 3,870,048 to Yoon discloses the use of elastic bands or rings in tubal ligation. The Yoon device is constructed so as to permit two or more ligating rings to be loaded at the same time, but discharged separately at different times and in succession to one another, even at different locations, all without removing the ligating device from the patient's body cavity. Yoon's device is also relatively complex.

U.S. Pat. No. 4,226,239 to Polk et al. also describes a surgical ligating instrument for tubal ligation within a human or animal body, by the application of two or more elastic ligating rings without the necessity of removing the instrument from the patient for each ligating ring. In the device of Polk et al., a number of ligating rings are stretched over a cylindrical shaft which is slidably and concentrically received within an outer cylindrical sleeve. As the cylindrical shaft is withdrawn proximally with respect to the outer sleeve, the outer sleeve successively forces the ligating rings off of the shaft, preferably one at time. The extent of relative motion between the shaft and the sleeve is controlled by a mechanical stop at the proximal end of the shaft, located in the pistol handle of the instrument. The surgeon can be sure that a only single band has been placed only if the mechanical stop is precisely calibrated to the width of an individual ligating ring. U.S. Pat. No. 4,860,746 discloses a device similar to that of Polk et al.

U.S. Pat. No. 5,207,690 to Rohrabacher et al. teaches that successive ligating rings may be slipped off of the cylindrical shaft onto which they have been preloaded by the use of separate forceps.

U.S. Pat. No. 5,269,789 to Chin et al. discloses a ligating band dispenser located at the distal end of an elongated introducer, which dispenser responds to manipulation of an operating structure at the proximal end of the introducer. The dispenser comprises first and second coaxially located, interfitted segments that support ligating bands at a plurality of axially spaced positions thereon. Each segment includes a spaced ligating band engagement structure for engaging portions of each ligating band or set of bands. One of the segments connects to the operating structure for being moved between first and second positions relative to the other of the segments. This motion dispenses one of the ligating bands from the distal end of the ligating instrument and moves the remaining ligating bands distally with respect to the dispensing means thereby to position a successive ligating band for being dispensed at a different site, as in some of the aforementioned devices as well. The Chin et al. instrument, however, is an improvement over those devices in that it is specially constructed to prevent more than a single ligating band from being dispensed in response to a single actuation of the operating structure. On the other hand, the ligating bands are initially greatly stretched when loaded onto the Chin et al. instrument, bringing about the necessity of a relatively strong spring in order to slide the bands distally. The surgeon's hand must work against this spring when actuating the device. Moreover, advancement of the ligating bands toward the dispensing end of the device requires the bands to be stretched even further than their initial stretched conditions. Such stretching requires even greater force to applied by the surgeon's hand. U.S. Pat. No. 5,356,416 to Chu et al. discloses a device similar to Chin et al. further including a sclerotherapy needle for administering a sclerotherapy agent as an alternative to ligating a lesion.

OBJECTS AND SUMMARY OF THE INVENTION

Therefore, it is an object of this invention to provide an instrument that can dispense plural ligating bands in sequence at discrete sites.

Another object of this invention is to provide a ligating instrument that can deposit plural ligating bands in sequence without requiring the instrument to be removed from a patient after each ligation.

Still another object of this invention is to provide a ligating band dispenser for attachment to diverse introducer structures including rigid and flexible endoscopes for ligating tissue.

The present invention permits multiple band firing without the need to retracting, reloading, and reinserting the dispenser. As a result, reintubation is required only after several ligating bands have been fired. Generally, a single intubation with the ligating band dispenser of the present invention is sufficient to ligate the tissue at at least one internal tissue site within a patient's body. This affords a savings in time and reduces patient discomfort during the procedure.

According to the invention, a ligating band dispenser located at the distal end of an elongated introducer responds to manipulation of an operating structure at the proximal end of the introducer. The dispenser supports a plurality of elastic ligating bands on a series of cylinders. An inner cylinder has proximal and distal portions and is adapted to support at least one ligating band in a stretched condition on or about its distal portion. An intermediate cylinder also has proximal and distal portions, and further has a distal end. The intermediate cylinder is positioned about or surrounding at least the proximal portion of the inner cylinder and is adapted to support at least another ligating band in a stretched condition on or about its distal portion. The inner and intermediate cylinders comprise axially sliding cylinders for dispensing the ligating bands. An outer cylinder which is removably attachable to the distal end of the elongated introducer, is positioned about or surrounding at least the proximal portion of the intermediate cylinder. The outer cylinder has a distal end into which the sliding cylinders slide. A trip wire is connected to the inner cylinder and extends proximally therefrom through the elongated introducer. The trip wire is adapted to cause an axially sliding motion of the sliding cylinders during an application of force to the trip wire. A restraining means is associated with each sliding cylinder to restrain sliding motion thereof during the application of force to the trip wire. Finally, a releasing means is provided to release the restraining means associated with one of the sliding cylinders upon the application of the pulling force. The released sliding cylinder slides in response to the applied pulling force while the distal end of either the intermediate or outer cylinder pushes the ligating band therefrom. According to this construction, at least two ligating bands may be independently dispensed onto tissue at one or more designated sites thereby accomplishing ligation thereof.

The intermediate cylinder may comprise a succession of intermediate cylinders, each of which is positioned about or surrounding the proximal portion of a preceding cylinder. Each of the succession of cylinders has at least a further ligating band thereabout. The successive cylinders are arranged so that they telescope sequentially with successive applications of pulling forces on the pull wire to push the ligating bands from one of the preceding and inner cylinders. According to this construction, a plurality of ligating bands may be independently dispensed onto tissue at one or more designated sites, for example, five ligating bands, without reloading the dispenser or the necessity of reintubating the patient.

The releasing means is preferably configured to release the restraining means associated with another of the sliding cylinders upon each successive application of the pulling force.

The dispenser also preferably includes complementary apertures and protuberances formed on adjacent ones of the inner, intermediate, and outer cylinders. The protuberances of one cylinder are received in the slots of an adjacent cylinder. The apertures have predetermined lengths such that the travel of each of the sliding cylinders is defined by the predetermined lengths of the apertures.

More generally, the ligating band dispenser may support a plurality of elastic ligating bands on a series of supporting members. A first support member has proximal and distal portions and is adapted to support at least one ligating band in a stretched condition about its distal portion. A second support member has proximal and distal portions, and further has a distal end. The second support member is positioned about or surrounding at least the proximal portion of the first support member and is adapted to support at least another ligating band in a stretched condition on or about its distal portion. The first and second support members comprise axially sliding support members for dispensing the ligating bands. A fixed member which is removably attachable to the distal end of the elongated introducer, is positioned about or surrounding at least the proximal portion of the second support member. The fixed member has a distal end into which the sliding support members slide. A trip wire is connected to the first support member and extends proximally therefrom through the elongated introducer. The trip wire is adapted to cause an axially sliding motion of the sliding support members during an application of force to the trip wire. A restraining means is associated with each sliding support member to restrain sliding motion thereof during the application of force to the trip wire. Finally, a releasing means is provided to release the restraining means associated with one of the sliding support members upon the application of the pulling force. The released sliding support member slides in response to the applied pulling force while the distal end of one of the second support and fixed members pushes the ligating band therefrom. According to this construction, at least two ligating bands may be independently dispensed onto tissue at one or more designated sites thereby accomplishing ligation thereof.

These and other features and advantages of the invention will be readily apparent from the following detailed description of certain embodiments taken in conjunction with the accompanying unscaled drawings.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 4 is a cross sectional view taken along line 4—4 in FIG. 3;

FIG. 5 is a cross sectional view taken along line 5—5 in FIG. 3;

FIG. 6 is an enlarged view of FIG. 3 showing the device in a partially activated state prior to delivery of a ligating band;

FIG. 7 is a cross sectional view taken along line 7—7 in FIG.6;

FIG. 13 is a cross sectional view of a fourth embodiment of a ligating instrument dispenser according to this invention, showing the device in assembled form and in a fully loaded state immediately prior to placement of a ligating band;

FIG. 14 is a cross sectional view taken along line 14—14 in FIG. 13;

FIG. 13A is a perspective view of one of the pull wires of FIG. 13;

FIGS. 15A-15C is a cross sectional view taken along line 15A, B, C-15A, B, C in FIG. 13, showing alternative lumen configurations for housing a tip wire and one or more pull wires for use with the embodiment of FIG. 13; and FIG. 16 is a cross sectional view of the embodiment of FIG. 13, now showing the device after delivery of a second ligating band;

FIG. 17 is a cross sectional view taken along line 17—17 in FIG. 15;

DETAILED DESCRIPTION OF SEVERAL EMBODIMENTS

Figure 1:
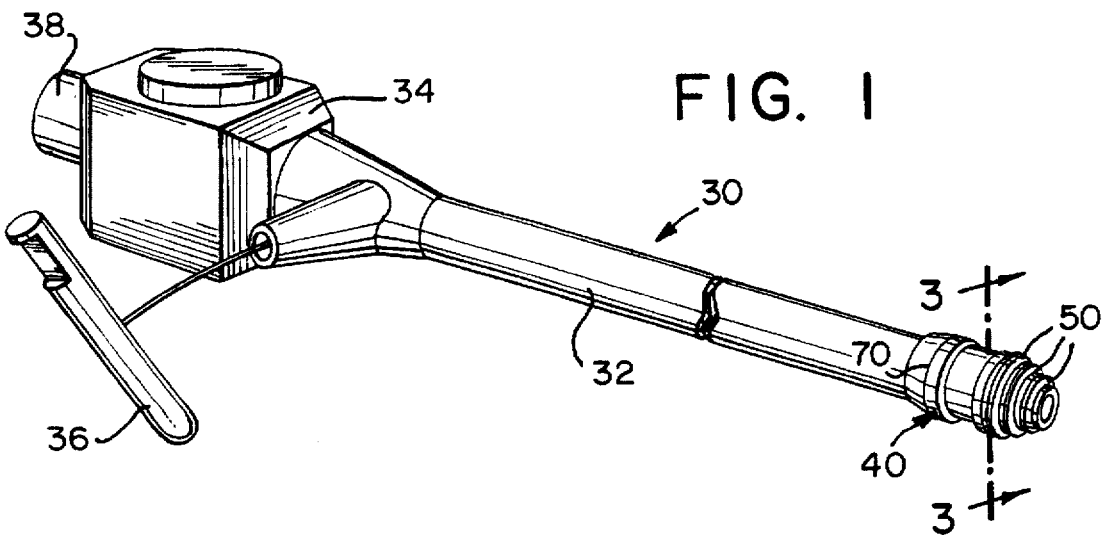
FIG. 1 is a perspective view of a first embodiment of a ligating instrument dispenser constructed in accordance with this invention.

FIG. 1 depicts, in perspective view, a first embodiment of a ligating instrument 30 that serially dispenses elastic ligating bands during a succession of operations by a surgeon. The ligating instrument 30 generally includes an introducer in the form of an elongated, rigid tubular housing 32. A proximal end portion 34 of the instrument 30 comprises a proximal actuator or controller 36 for causing a ligating band to be dispensed by the instrument 30. The housing 32 is formed in a hollow tubular form to provide a central or axial passage that communicates a proximal vacuum connection 38 to a distally mounted ligature dispenser 40, as will be explained in greater detail below.

The proximal controller 36 is connected to the dispenser 40 by a pull or trip wire that passes through a proximal seal (not shown) located within the proximal end portion 34 of the instrument 30. Variations of such a proximal actuator and pull wire operating structure have been incorporated in ligating instruments. The specifically disclosed embodiment is merely representative of such diverse implementations.

The proximal seal referred to above allows suction to be applied by the vacuum connection 38 and the central passage of the instrument to and through the dispenser 40, while allowing proximal manipulation of the trip wire. With such a proximal seal in place, suction applied to the vacuum connection 38 draws tissue into the dispenser 40 for ligation, as will be made clear below.

While a specially designed ligating instrument 30 has been illustrated, it will be readily apparent to those of ordinary skill in the relevant art that the dispenser 40 may be connected, such as by a friction fit, to the end of a conventional endoscope having a central lumen therethrough and access ports at the proximal working end to permit the application of suction and the passage of a trip wire externally of the endoscope handle. In such a case, the surgeon may simply pull on the trip wire itself to deliver a ligating ring, or she may attach a clamp of any suitable kind to the trip wire, for ease of manipulation. None of these differences affects the scope of the present invention, which is directed to the construction and operation of dispenser 40 itself.

The ligating instrument 30 or a conventional endoscope may further include means for providing visualization of internal body tissue distal of the dispenser 40, such as a conventional fiber optic and lens arrangement (not shown) or the like. In use, such visualization means generally assists the surgeon in guiding the dispenser 40 to the desired tissue site to be ligated.

Figure 2:
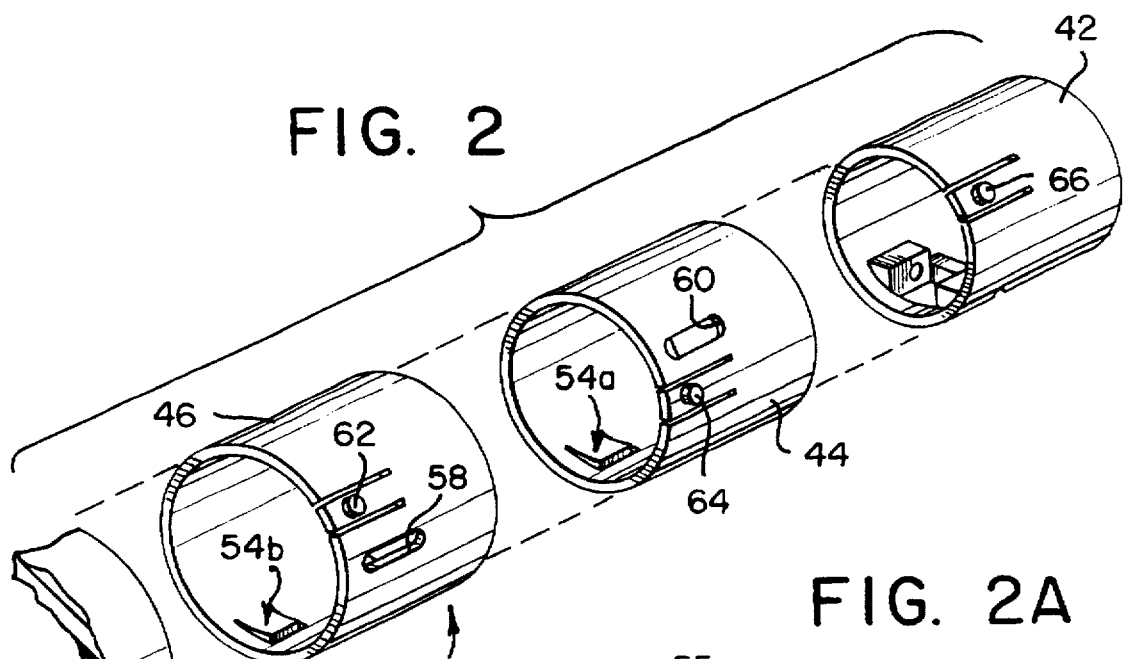
FIG. 2 is an exploded, perspective view of the dispenser of the embodiment of FIG. 1 showing several slidably mounted cylinders in spaced relation to one another and their spring tab-type locking mechanisms.

Referring generally to FIGS. 2 though 8, in which like component parts are consistently numbered for ease of reference, the component parts and manner of assembly of a first embodiment of the dispenser 40 of the ligating instrument 30 of FIG. 1 are shown in detail.

First Embodiment

FIG. 2 shows an exploded, perspective view of the dispenser 40. In the illustrated embodiment, the dispenser 40 comprises four telescoping support members, illustrated as cylinders, three of which are axially slidably mounted and have ligating bands or rings 50 disposed thereon. The axial movable cylinders include, in radial succession (as shown from right to left), an inner cylinder 42 and first and second intermediate cylinders 44, 46. The ligating bands 50a, 50b, and 50c are disposed on or about a distal portion of these cylinders, respectively (see FIG. 2B). The ligating bands 50 are preferably formed of isoprene and are circular having a generally square solid body cross section. So formed, each band 50 has a flat, smooth inside surface 52 for mounting on the cylinders 42, 44, and 46. An outer cylinder 48, shown broken away in FIG. 2, is rigidly coupled to the housing 32. As illustrated, the outer diameter of each cylinder and the inner diameter of an adjacent cylinder are chosen so that the annular gap therebetween is sufficient to permit unrestricted or free sliding of the cylinders, yet insufficient to permit the ligating bands 50 to fit or be pinched therebetween when pushed therefrom, as explained more fully below.

According to one aspect of the invention, the ligating bands 50 are successively dispensed by releasing a lock mechanism 54 that restrains axial, telescoping movement of a cylinder (supporting the ligating band) into an adjacent cylinder. As used herein, a "lock mechanism" refers to a mechanism that provides a positive stop on the dispenser 40 whereby a single ligating band is dispensed with a single actuation of an actuator, such as the proximal controller 36. In the embodiment of FIGS. 3–8, the lock mechanism comprises spring tabs 54a, 54b, and 54c adapted to normally project radially inwardly in their relaxed state to impede proximal sliding motion of cylinders 42, 44, and 46. The spring tabs 54 may be formed integral to the first and second intermediate cylinders and the outer cylinder, respectively, when the cylinders are formed by, for example, an injection molding process. Alternatively, a region of material that outlines the spring tabs 54 may be removed on three sides thereof to define the spring tabs 54, for example, using a slitting saw, and then plastically deforming the cut out spring tabs 54 about a wrapping tool or the like by a cold bending process to reliably impart a curve within prescribed tolerances sufficient to form the lock mechanism function as previously described, and as shown in FIGS. 2 and 2B.

Figure 2A:
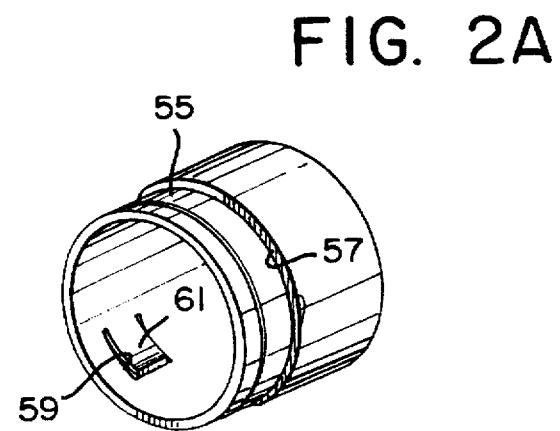
FIG. 2A is a perspective view of a modified dispenser of FIG. 1 in which the locking mechanism is a spring.
Figure 2B:
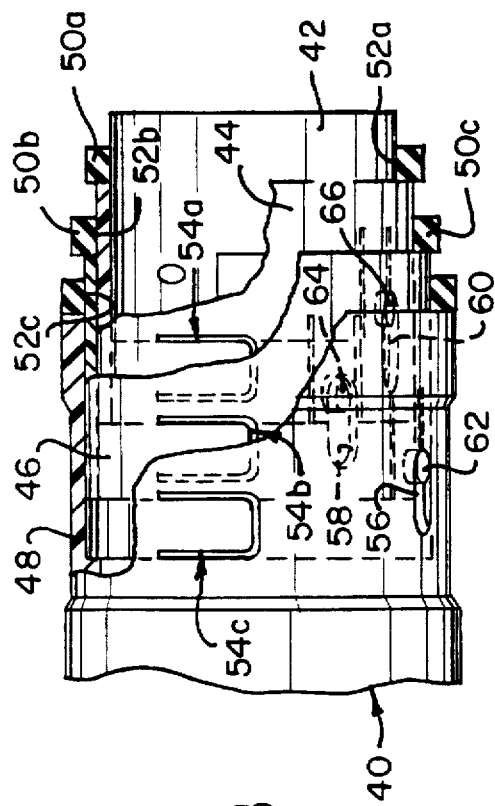
FIG. 2B is a bottom view, partially broken away, of the embodiment of FIG. 1.

In FIG. 2A, a perspective view of a modified lock mechanism 54A is shown with some parts rotated and other parts omitted for clarity. The lock mechanism 54A comprises an arcuate spring element 55 preferably located in an annular slot 57 formed in each of the outer 48 and first and second intermediate 44, 46 cylinders. The spring element 55 may be made by conventional spring forming techniques. The cylinders are provided with a slot 59 which is in register with the annular slot 57. A curved tip portion 61 of the spring element 55 is adapted to project through the slot 59 and extend into the cylinders 44, 46, and 48 in the same manner as the spring tabs 54 to provide a lock mechanism to restrain proximal motion of the assembled cylinders (see, for example, FIGS. 2B and 3).

The extent of axial travel of the cylinders 42, 44, 46 are limited by axial slots 56, 58, 60 in adjacent cylinders. With reference now to FIGS. 2 and 2B, the latter of which shows a bottom view, partially broken away, of the assembled dispenser 40, the axial restraint mechanism can be better appreciated. The outer cylinder 48 has an axial slot 58 that receives a protuberance 62 extending radially outwardly from the second intermediate cylinder 46 to interlock the two cylinders. Likewise, the second intermediate cylinder 46 has an axial slot 60 which receives a protuberance 64 extending radially outwardly from the first intermediate cylinder 44 to interlock those two cylinders. Finally, the first intermediate cylinder 44 has an axial slot 60 which receives a protuberance 66 extending radially outwardly from the inner cylinder 42 to interlock those two cylinders. Alternatively, any pair of the previously described slots 56, 58, 60 and protuberances 62, 64, 66, respectively, could be located in reverse, that is with radially inwardly extending protuberances engaging a suitably positioned slot, and still achieve the aforementioned interlocking of the cylinders 42, 44, 46 and 48. In the preferred embodiment, the slots 56, 58, and 60 are circumferentially displaced or offset, for example, by thirty degrees, to add structural integrity to the dispenser 40 and to better ensure that the relative alignment of the cylinders 42, 44, 46, and 48 remains intact. Relative motion among the cylinders can be limited, restrained, or both, in other ways, as can be readily appreciated. Each of the protuberances is mounted on a flexible tab to facilitate assembly of the dispenser 40. In the fully loaded, initial state of FIGS. 1 to 5, each of protuberances 62, 64, 66 is maintained at the distal end of a respective slot 56, 58, 60 by the circumferentially directed spring tabs of the lock mechanism 54, described in further detail below. Except for FIG. 8, the slots 56, 60, and 62 and protuberances 58, 64, and 66 have been omitted for clarity.

Figure 3:
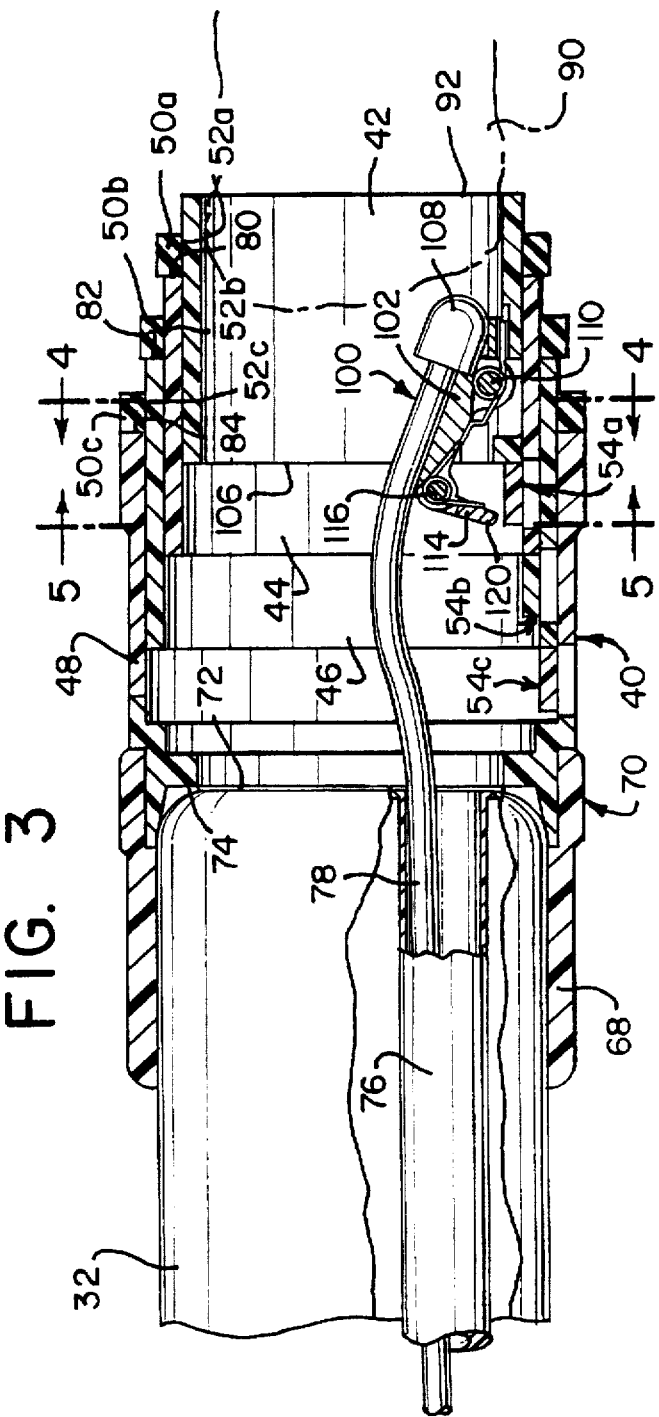
FIG. 3 is a cross sectional view taken along line 3—3 of FIG. 1, showing the device in assembled form and in a fully loaded state immediately prior to placement of a ligating band.

Referring now to FIG. 3, and also simultaneously to cross-sectional views shown in FIGS. 4 and 5, the dispenser 40 is shown in its assembled, fully loaded and initial state of operation. Tubular housing 32 of the ligating instrument 30 is shown, broken away, for the sake of clarity. In practice, a proximal cylindrical portion 68 of a cap 70 is frictionally engaged about tubular housing 32, with the distal end face 72 of tubular housing 32 abutting a boss or mounting stop 74 in cap 70. Alternatively, cap 70 and housing 32 may be secured together by other means, for example, an adhesive. The cap 70 may be formed of substantially transparent polycarbonate, or of another, flexible material suitable for establishing a friction fit over the distal end face 72 of the tubular housing 32. The endoscope has a biopsy channel 76 extending to the proximal end 34. The biopsy channel 76 (or another channel that extends from end to end) contains a trip wire 78 used to dispense the ligating bands 50a, 50b, and 50c.

Ligating band 50a is stretched over and about the distal end of inner cylinder 42 so that its flat surface 52a is along the exterior surface of the inner cylinder 42 and is positioned so that the distal end 80 of the first intermediate cylinder 44 abuts the ligating band 50a. The ligating band or ring 50b is similarly stretched over and about the distal end of the first intermediate cylinder 44 and abuts a distal end 82 of the second intermediate cylinder 46. Finally, ligating ring 50c is stretched over and about the second intermediate cylinder 46 and abuts a distal end 84 of the outer cylinder 48. A lubricous coating or other surface contour may be interposed between a ligating band and its supporting cylinder or, more generally, supporting member. Manipulation of the proximal controller 36 by a surgeon enables the successive firing of the bands 50a, 50b, and 50c onto any tissue 90 that may be drawn into a hollow distal end 92 of the dispenser 40 by suction, as described below. The proximal controller 36 is linked to the telescoping cylinders 42, 44, 46, and 48 by the trip wire 78 and a release mechanism 100.

The release mechanism 100 comprises a pivot 102 which is secured to the inner cylinder 42 and is axially movable therewith in a proximal direction (to the left in the figure) when the spring tab 54a of the first intermediate cylinder 44 is displaced radially outwardly to a position clear of the proximal end 106 of the inner cylinder 42. Manipulation of the proximal controller 36 provides tension in the trip wire 78. The trip wire is anchored to the pivot 102 by a trip wire anchor 108 secured in an aperture or notch, such that the tensioned trip wire 78 causes the pivot 102 to rotate about a pivot pin 110 against the restoring force of a pivot spring 112. The pivot spring 112 nominally biases the pivot 102 in a locked position whereby the locking spring tab 54a prevents axial motion of the cylinder 42 and the dispensing of ligating band 50a. As the pivot 102 rotates about pivot pin 110, a pivot arm or "bird's beak" 114 presses upon the spring tab 54a to cause the same to displace radially outwardly. When the spring tab 54a has been displaced so that the proximal end 106 of the inner cylinder 42 is clear of the tab 54a (see FIG. 7), the tensioned trip wire 78 draws the inner cylinder 42 proximally. Meanwhile, the distal end 80 of the first intermediate cylinder 44 restrains proximal motion of the ligating band 50a as the inner cylinder 42 is telescoped proximally under the flat surface 52a. Continued proximal motion forces the band 50a distally off of the inner cylinder 42 and of the dispenser 40 onto or over the tissue 90 thereby accomplishing ligation thereof (see FIG. 8). The ligating bands 50b and 50c remain loaded for subsequent placement at the same (or different) location as the ligating band 50a. The tissue 90 may be a varix, an internal hemorrhoid, or other internal body structure, as the case may be.

Figure 8:
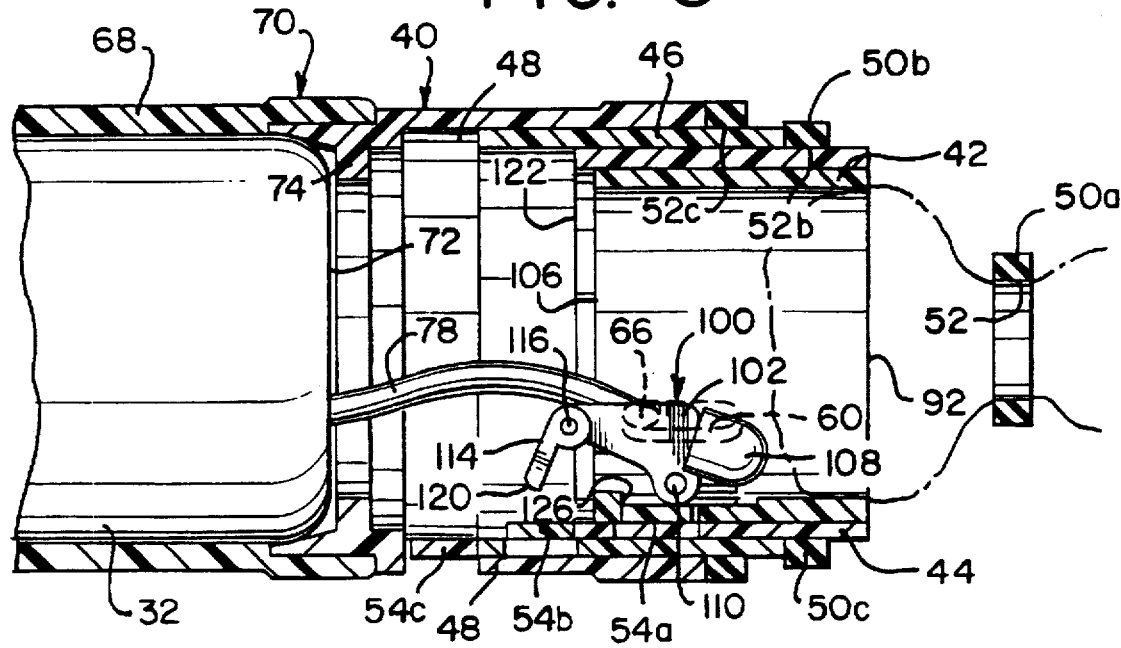
FIG. 8 is now showing the device immediately after delivery of a ligating band.

To prevent the firing of multiple ligating bands with a single manipulation of the proximal controller 36, the pivot arm 114 is coupled to the pivot 102 by a trailing link which comprises a pivot arm pin 116 and a pivot arm spring 118. FIG. 6 illustrates the dispenser 40 in a fully loaded yet intermediate or transient position during the telescoping of the inner cylinder 42 just prior to placing ligating band 50a. As shown in FIG. 6, the trailing link enables the pivot arm 114 to depress the spring tab 54a sufficient to clear the proximal end 106 of the inner cylinder 42, yet ensures that a pivot arm tip 120 folds under (or drags behind) the pivot 102 with the proximal movement of the release mechanism 100 with each telescoping cylinder. Preferably, the surgeon or other person manipulating the proximal controller 36 applies a steady pull to the trip wire 78 once the tissue 90 is aspirated into the dispenser 40. The pivot arm tip 120 folds under the pivot 102 as the pivot 102 is towed proximally by the force applied to the trip wire 78. When the pulling force is released from the trip wire 78, the pivot arm tip 120 returns to its nominal, unfolded rest position, as shown in FIGS. 3 and 8. As a result, the pivot arm tip 120 engages the lock mechanism 54 of only one cylinder with each actuation of the proximal controller 36.

It has been empirically determined that the pulling force on the trip wire 78 may cause a mild elastic stretching of the trip wire until such a time that a force sufficient to overcome the static frictional seating of the ligating band 50 has been provided. Only after a force sufficient to release the static frictional seating and cause movement of the sliding cylinder (42, 44, or 46) has been applied, will that cylinder move or snap into a surrounding cylinder. Until such time, however, an elastic force may develop in the trip wire 78 in the direction of the pulling force. Ultimately, the pulling force and elastic force will overcome the break away friction required to displace the ligating band 50 from the sliding cylinder (42, 44, or 46). At this moment, the elastic force will temporarily provide a force that is greater than the ligating band's coefficient of dynamic friction so that the proximal movement of the sliding cylinder is maintained even if the pulling force is released. The proximal movement of the sliding cylinder draws the distal attachment point of the trip wire 78 toward the proximal controller 36 and thereby releases the elastic stretch of the trip wire 78, if any. The energy stored in the elastically stretched trip wire, if stretched, precludes any "half-pull" condition, in which the operator or surgeon may release the pulling force from the trip wire 78 prematurely, that is, after the sliding cylinder has been released but prior to displacing the ligating band. As a result, there is little or no risk that a half-pull condition will result in which the trip wire 78 has been pulled without causing a ligating band to be dispensed or allowing a subsequent pull to result in two bands being fired.

According to the invention, the lock mechanism provides a positive stop which precludes the possibility of firing multiple ligation bands 50 with a single actuation of the proximal controller 36 and which permits the surgeon to apply a steady force to the trip wire 78 with confidence that only one ligating band will be dispensed. Nevertheless, to further reduce the risk of misfiring, and as a modification of the foregoing, the travel of the cylinders may be tailored to decrease the likelihood that the pivot arm tip 120 (which is axially repositioned with the telescoping movement of the inner cylinder 42) will engage more than one spring tab 54. For example, the total axial movement of the trip wire 78 to dispense the ligating band 50a may be less than that required to dispense the ligating band 50b, and the axial movement of the trip wire 78 to dispense the ligating band 50b may be less than that required to dispense the ligating band 50c.

In FIG. 6, the pivot arm tip 120 engages the spring tab 54a of the first intermediate cylinder 44 to permit the inner cylinder 42 to telescope into the intermediate cylinder 44 and thereby dispense the ligating band 50a, as previously described. This trailing link reliably releases the lock mechanism 54 of the cylinder that is closest to the innermost, loaded cylinder, which in the illustration of FIG. 6 is the inner cylinder 42. Further, by the construction of the release mechanism 100, including the trailing linkage on the bird's beak, the surgeon is assured that only a single ligating ring has been dispensed by dispenser 40 of the ligating instrument 30. Also, the dispenser 40 is adapted so that the pivot arm tip 120 is positioned over the spring tab 54b (see FIG. 8) once the ligating band 50a has been dispensed and the inner cylinder 42 telescoped into the first intermediate cylinder 44. Until the tension to the trip wire 78 is released, the trailing link maintains the bird's beak distal to the lock mechanism of the next loaded cylinder (see FIG. 6, where the bird's beak 120 has moved proximally with the dispensing of the ligating band 50a, but remains distal to the next lock mechanism 54b. Accordingly, the release mechanism 100 will release spring tab 54b upon subsequent actuation of the proximal controller 36 so that ligating band 50b can be dispensed, and so on, until the last (outermost) ligating band is dispensed.

Preferably, the dispenser 40 is mounted onto the tubular housing 32 such that the release mechanism 100 is rotationally aligned with the biopsy channel 76 or other channel through which the trip wire 78 extends. The proximal cylindrical portion 68 of the cap 70 of the dispenser 40 may include an alignment marker to assist in this preferred rotational alignment.

In FIG. 7, the pivot arm tip 120 is shown having a portion 121 that extends from the tip 120 to contact the lock mechanism 54 with a reduced frictional coefficient, as by shaping or coating the portion 121.

In order to place a ligating band on a varix, internal hemorrhoid, or other internal body structure, as the case may be, the distal end of the instrument is positioned adjacent such tissue in conventional manner. Suction is then applied via vacuum connection 38. In this way, the tissue 90 to be ligated is drawn within central bore 92 of the dispenser 40 as shown in dotted lines in FIG. 3. In this position, the instrument may be actuated to place a ligating band 50 (first ligating band 50a) on the tissue to achieve ligation, as will now be explained with reference to FIG. 8. Inner and intermediate cylinders 42, 44, and 46, like all other components of the instrument 30, include a hollow central passage for the application of suction at the distal end of the device. Upon the next successive actuation of the ligating device, band 50b will be dispensed, and then band 50c, and so on.

FIG. 8 illustrates the dispenser 40 immediately after delivery of the first ligating band 50a onto tissue 90. The delivery of the ligating band 50a caused the inner cylinder 42 to telescope into the first intermediate cylinder 44 until the protuberance 66 reached the proximal end of the slot 60 and caused the trailing link to fold under the pivot 102. The tension applied to the trip wire 78 to dispense the ligating band 50a has been released in FIG. 8, as seen by the upright (normally biased) position of the bird's beak 114. Subsequent manipulation of the proximal controller 36 again causes the pivot arm tip 120 to release the lock mechanism of the innermost, loaded cylinder, which is now the spring tab 54b of the second intermediate cylinder 44. Once the spring tab 54b is depressed clear of a proximal edge 122 of the first intermediate cylinder 44, the first intermediate cylinder (along with the inner cylinder 42 and the release mechanism 100) telescopes into the second intermediate cylinder 46 to dispense the ligating band 50b. As with the dispensing of ligating band 50a, the trailing link precludes dispensing additional ligating bands by folding over so as to not release the lock mechanism of the next loaded cylinder (which, in this illustration, is cylinder 46 with ligating band 50c thereabout).

The dispenser 40 could be modified so that the spring tabs 54 secure the nested or telescoped cylinders together. In FIG. 8, the nested inner cylinder 42 is secured to the first intermediate cylinder 44 by the engagement of the spring tab 54a of the latter to an aperture 126 of the former. In particular, once the pivot arm tip 120 has engaged the lock mechanism 54a and has depressed the spring tab 54a sufficient to clear the proximal end 106 of the inner cylinder 42, the proximal end 106 of the inner cylinder 42 slides into the first intermediate cylinder 44 against the resilient restoring force of the spring tab 54a which may be adapted to project into the space occupied by the inner cylinder 42. When the inner cylinder 42 is slid proximally a distance sufficient to dispense the ligating band 50a, the spring tab 54a is clear to return to its relaxed state within the aperture 126, just distal to the proximal end 106 of the inner cylinder 42. Likewise, the second intermediate cylinder 46 can be secured to the inner and first intermediate cylinders by engagement of spring tab 54b into the radially inwardly projecting space immediately below and in register with the spring tab 54a. Each of the cylinders in a particular construction of the dispenser 40 can be similarly secured once the cylinders are telescoped. However, alignment of the locking mechanism 54 of each cylinder is not critical to the invention nor to the structural integrity of the dispenser 40.

The presently preferred inside/outside diameters of the cylinders in the three telescoping cylinder embodiment of FIGS. 1–8 are (with +0.005 inch tolerances) as follows: for the inner cylinder are 0.365/0.414 inches, for the first intermediate cylinder are 0.418/0.448 inches, and for the second intermediate cylinder are 0.452/0.482 inches. The presently preferred dimensions of ligating bands 50a, 50b, and 50c in the unstretched condition are as follows: 0.1875 inch outside diameter, 0.0625 inch inside diameter, and 0.0625 inch axial length. When positioned on or about the distal portion of the sliding cylinders 42, 44, and 46, the ligating bands 50a, 50b, 50c are typically stretched about eight to ten times their nominal, unstretched inside diameters. As can be appreciated, the force nominally required to displace or deploy the ligating band 50a mounted on the inner cylinder is less than that required to displace or deploy the ligating band 50c mounted on the second intermediate cylinder. The application of a suitable displacement force to the dispenser 40, regardless of the aforementioned lock mechanism 54, preferentially favors the release of the ligating bands in the following order: 50a, 50b, and then 50c. The dispenser 40 is inherently adapted to preferentially favor the firing of one band before another, and may further include coatings or varied surface configurations on the outside surfaces of the telescoping cylinders to further enhance a desired order of band fling, for example, from the innermost support member to the outermost support member. Either treatment functions to reduce the relative frictional forces of removing a given band 50 from the outer surface of one of the telescoping cylinders. Alternatively, certain of the bands 50 can be adapted to have a relatively higher frictional seating on the outside surface of the telescoping cylinders, for example, by increasing the axial length of the band so that it contacts a greater portion of the cylinder or support member surface. The cylinders 42, 44, and 46 preferably have respective overall lengths as follows: 0.327 inches, 0.342 inches, and 0.357 inches. The outer cylinder 48 preferably has a 0.486 inch inside diameter, 0.542 inch outside diameter, and 0.406 inch axial length. The proximal cylindrical portion 68 of the cap 70 of the dispenser 40 preferably extends 0.381 proximal of the outer cylinder 48 for a friction fit to the tubular housing 32.

Second Embodiment

Figure 9:
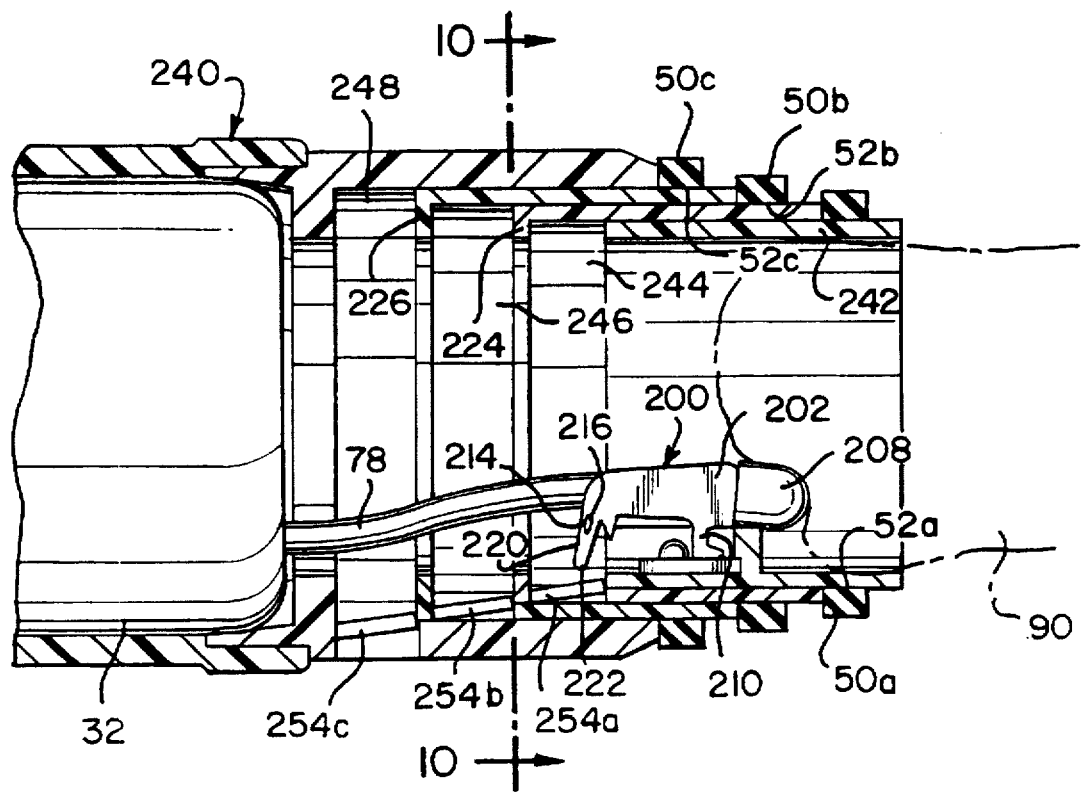
FIG. 9 is a cross sectional view of a second embodiment of a ligating instrument dispenser according to this invention, showing the device in assembled form and in a fully loaded state immediately prior to placement of a ligating band.
Figure 10:
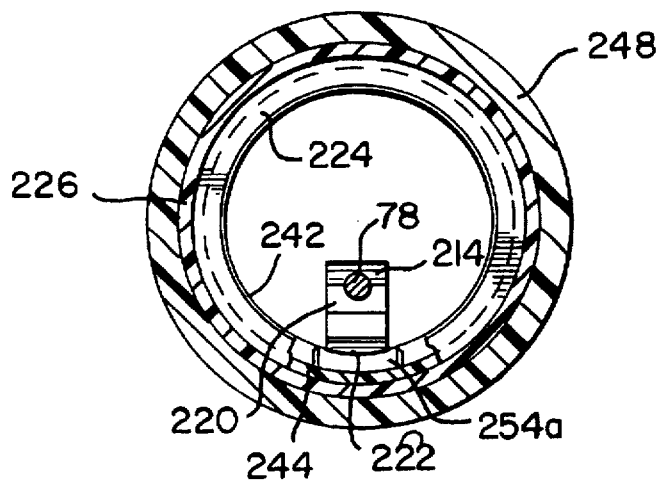
FIG. 10 is a cross sectional view taken along line 10—10 in FIG. 9.
Figure 11:
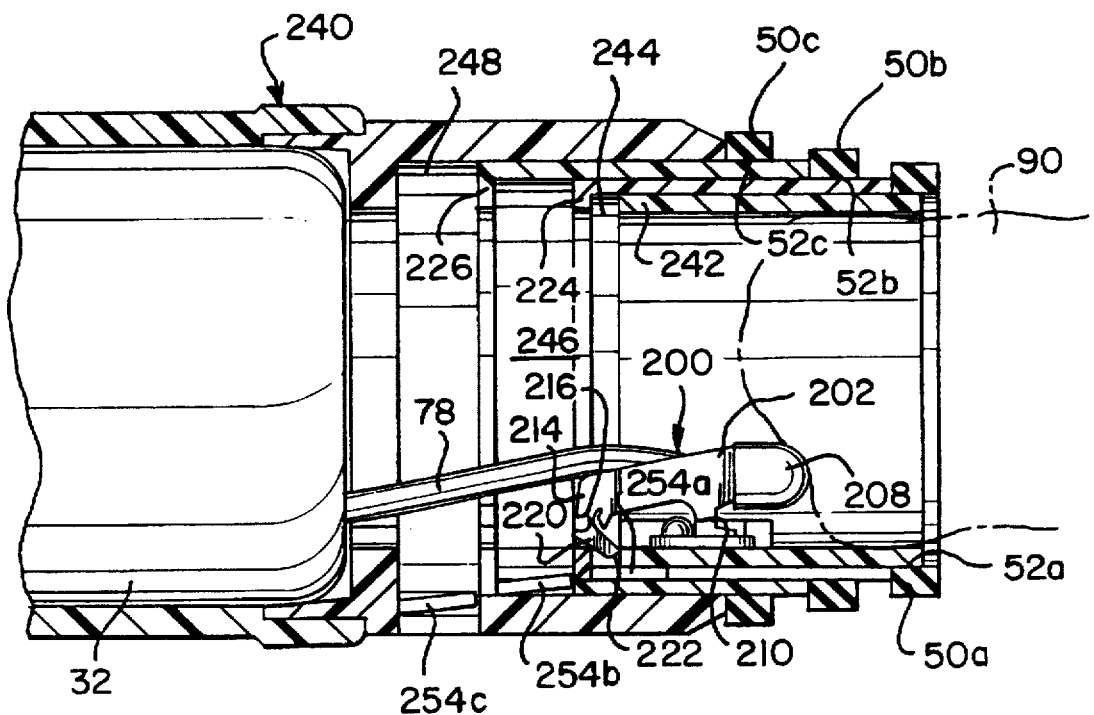
FIG. 11 is a cross sectional view of the embodiment of FIG. 9 showing the device in a partially activated state just prior to firing a ligating band.

In FIGS. 9–11, a second embodiment of a ligating instrument dispenser 240 constructed in accordance with this invention is illustrated. In this second embodiment, the lock mechanism 254 comprises axially directed spring tabs 254a, 254b, and 254c to restrain the dispensing of ligating bands 50a, 50b, and 50c, respectively. In FIG. 9, the dispenser 240 is shown in its assembled form on the housing 32 and in a fully loaded state immediately prior to placement of the ligating band 50a. In this second embodiment, the proximal controller 36 is linked by the trip wire 78 to a release mechanism 200 which permits the cylinders 42, 44, 46, and 48 to telescope and thereby dispense the ligating bands 50.

The release mechanism 200 is simpler in construction than the release mechanism 100 of FIGS. 3–8. It comprises a pivot 202 which is secured to the inner cylinder 242 by a "living hinge" 210. Living hinges are known in the art and generally comprise a resiliently flexible material hingedly lining two elements together. Preferably, the living hinge 210 is integrally formed with (for example, by an injection molding process) and disposed between the inner cylinder 242 and the pivot 202. The release mechanism 200 also includes a pivot arm 214 hingedly connected to the pivot 202 by a hinge 216, which is also preferably a living hinge in this embodiment. A bird's beak 220 having a camming surface 222 permits the bird's beak to fold radially inward (in a counter-clockwise direction) when it contacts the upstanding (radially inwardly extending) walls 224, 226 of the first and second intermediate cylinders 244, 246, respectively, as the pivot 202 is withdrawn proximally. FIG. 11 shows the dispenser 240 in a partially activated state just prior to firing a ligating band.

In operation, the complementary lock mechanism 254 and release mechanism 200 operate in the same way as the lock and release mechanism 54, 100 of the embodiment of FIGS. 3–8 to ligate a tissue 90. In particular, manipulation of the proximal controller 36 provides tension in the trip wire 78. The trip wire is anchored to the pivot 202 by a trip wire anchor 208 in an aperture or notch such that the tensioned trip wire 78 causes the pivot 202 to rotate about the living hinge 210, the living hinge 210 being naturally formed (nominally biased) to rest in a state such that the beak 220 is clear of contact of the lock mechanism 254 (see FIG. 9). The locking spring tab 254a prevents axial motion of the cylinder 242 and the dispensing of ligating band 50a (see FIG. 10) when the beak 220 is in its rest state. As the pivot 202 rotates about living hinge 210, the bird's beak 220 presses upon the spring tab 254a to cause the same to displace radially outwardly. When spring tab 254a has been displaced so that the proximal end 206 of the inner cylinder 242 is clear of the tab 254a (see FIG. 11), the tensioned trip wire 78 draws the inner cylinder 242 proximally. Meanwhile, the distal end 280 of the first intermediate cylinder 244 prevents the ligating band 50a from moving proximally with the telescoping motion of the inner cylinder 242. Continued proximal motion forces the flat surface 52a of the ligating band 50a distally off of the inner cylinder 242 and of the dispenser 240 onto or over the tissue 90 thereby accomplishing ligation thereof, as shown in FIG. 8 in connection with the first embodiment. The ligating bands 50b and 50c remain loaded for subsequent placement at the same (or different) location as the ligating band 50a. As previously noted, the dispenser 240 is designed to preferentially dispense the ligating band on the innermost, loaded telescoping cylinder before any other cylinder.

The hinge 216 operates as a trailing link, in a similar manner as the pivot arm assembly 114, 116, 118 of the previous embodiment, to prevent multiple band firing or dispensing with a single manipulation of the proximal controller 36. As shown in FIG. 11, the trailing link enables the pivot arm to depress the spring tab 254a sufficient to clear the proximal end 206 of the inner cylinder 242, yet ensures that the beak 220 folds under (or drags behind) the pivot 202 with the proximal movement of the release mechanism 200 with each telescoping cylinder. As a result, the beak 220 engages the lock mechanism 254 of only one cylinder with each actuation of the proximal controller 36, as previously described. In FIG. 11, the beak 220 engages the spring tab 254a of the first intermediate cylinder 244 to permit the inner cylinder 242 to telescope into the intermediate cylinder 244 and thereby dispense the ligating band 50a. This embodiment of the trailing link incorporating a living hinge 216 reliably releases the lock mechanism 254 of the cylinder that is closest to the innermost, loaded cylinder, which in the illustration of FIG. 11 is the inner cylinder 242. Further, by the construction of the release mechanism 200, including the trailing linkage on the pivot arm 214, the surgeon is assured that only a single ligating ring is dispensed by dispenser 240 with a single pull of the proximal controller 36.

The resultant delivery of each ligating band 50 is substantially as shown in FIG. 8; the structural differences from the previously described embodiment have no material impact on the operation of the dispenser 240.

Third Embodiment

Figure 12:
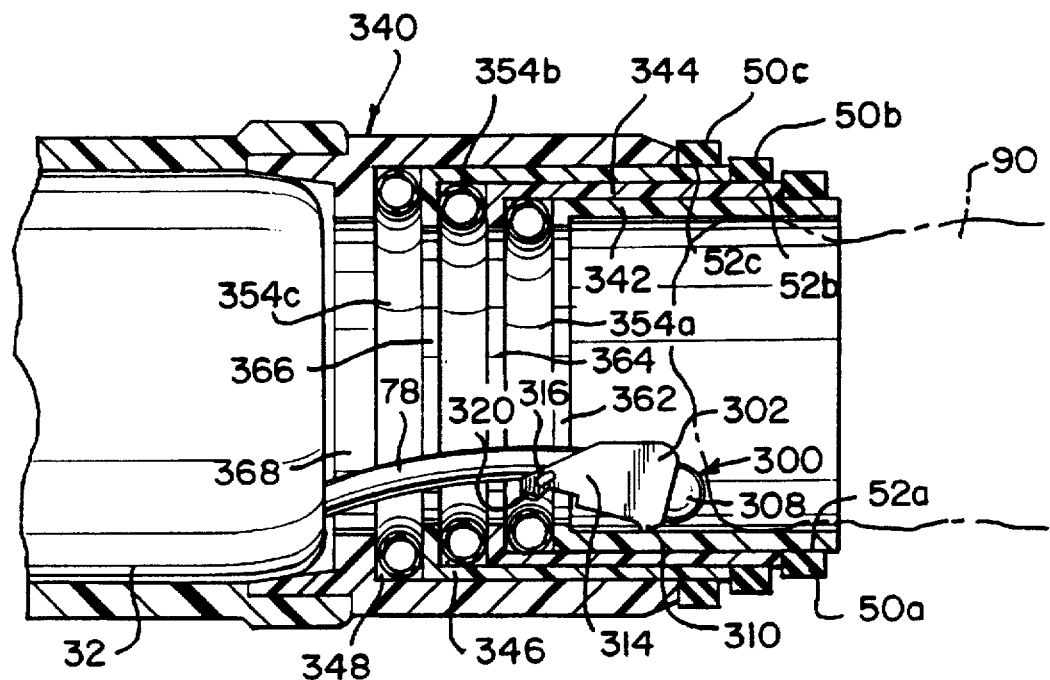
FIG. 12 is a cross sectional view of a third embodiment of a ligating instrument dispenser according to this invention, showing the device in assembled form and in a fully loaded state.
Figure 12A:
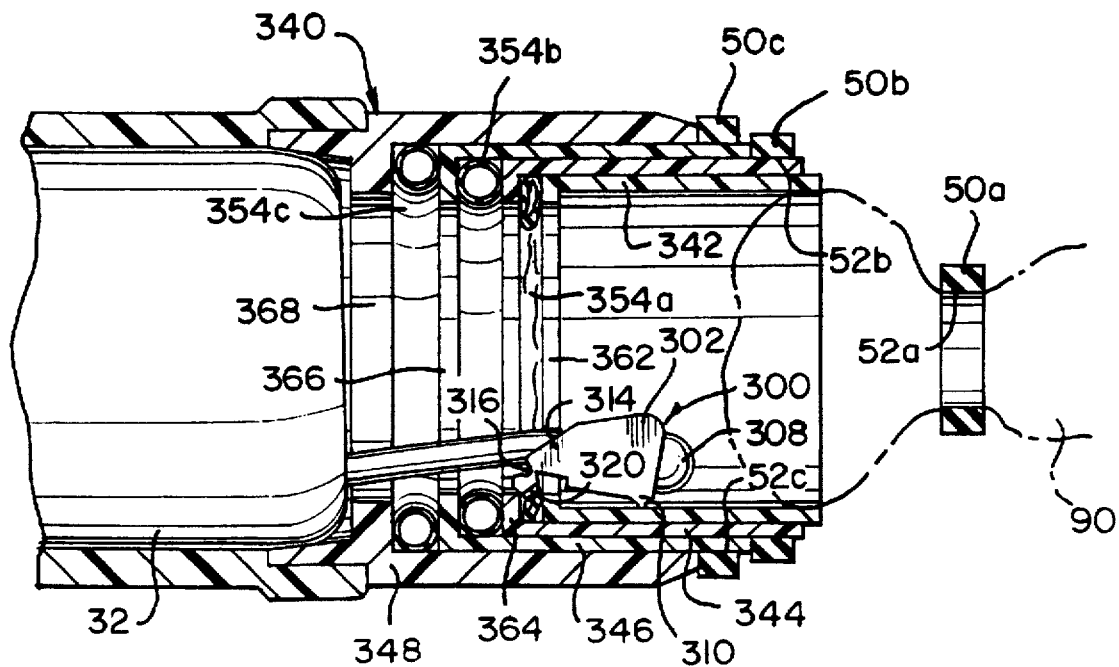
FIG. 12A is a cross sectional view of the embodiment of FIG. 12 in an actuated state just after dispensing a ligating band.

FIG. 12 illustrates a third embodiment of a ligating instrument dispenser 340, constructed in accordance with this invention, in a fully loaded state prior to dispensing any ligating bands 50. In this embodiment, the lock mechanism comprises expanded (or perhaps inflated) toroidal bags 354 which are positioned between the telescoping cylinders to axially space the cylinders by at least approximately the width of a ligating band 50. The toroidal bags 354 may be placed in an expanded state by filling with a liquid or gas (at either atmospheric or superatmospheric pressures), as appropriate for the particular body passageway being ligated (for example, air may be used to expand the toroidal bags 354 when the dispenser is used in the esophagus, whereas saline may be used when the dispenser is used in a tubal ligation procedure). Cylinders 342, 344, 346, 348 are provided with radially inwardly extending walls 362, 364, 366, 368, respectively, which are seated against the expanded toroidal bags 354. Together, the expanded toroidal bags 354 and the walls 362, 364, 366, 368 of this embodiment comprise a positive stop that restrains the cylinders from nesting or firing multiple ligation bands 50 with a single actuation of the proximal controller 36. Because the expanded toroidal bags 354 have an axial length of approximately the same magnitude as the ligating bands 50, the expanded toroidal bags 354 not only restrain proximal motion of the cylinders, but also prevent inadvertent dispensing of more than one ligating band 50. Only when the toroidal bag 354 is permitted to change to an unexpanded state, can a cylinder move proximally and thereby dispense a ligating band 50. In FIG. 12A, toroidal bag 354 is shown in an unexpanded state with the inner cylinder 342 partially nested in the first intermediate cylinder 344 after having dispensed the first ligating band, band 50a.

A release mechanism 300 similar in construction to the release mechanism 200, which has previously been described in detail, includes a beak 320 including a surface adapted to puncture a toroidal bag 354 when a pivot 302 is rotated with respect to the inner cylinder 342 about a living hinge 310. In its nominal rest position, the beak 320 is clear of contact of the toroidal bags 354. The beak 320 is preferably connected to the pivot arm 314 by a living hinge 316 which nominally orients the beak 320 toward the toroidal bags 354 for puncturing same when the trip wire 78 is pulled and the pivot 302 rotates. The hinge 316 folds the beak 320 radially inward (in a counter-clockwise direction) upon contact with any of the upstanding walls 364, 366, 368 of the first intermediate, second intermediate, and outer cylinders 344, 346, 348, respectively (see FIG. 12A).

In use, the complementary lock mechanism 354 and release mechanism 300 function as do the previously described lock and release mechanisms to ensure that a single ligating band 50 is dispensed with a single actuation of the proximal controller 36. The movement of the cylinders and the mounting of the ligating bands 50 is substantially as previously described; accordingly, the following discussion pertains to the specifics of the lock mechanism 354 and the release mechanism 300 as employed in this embodiment.

When a surgeon manipulates the proximal controller 36 to apply a proximal pulling force (to the left in the figure) to the trip wire 78 a pivot arm 314 is caused to rotate counter-clockwise which in turn causes the beak 320 to engage and puncture the toroidal bag 354. In FIG. 12A, the beak 320 has punctured the toroidal bag 354a. Immediately after the toroidal bag 354a is punctured, the pulling force entrains the inner cylinder 342 proximally (by virtue of its attachment to the release mechanism 300) to dispense the ligating band 50a and ligate the tissue 90, as previously described. The punctured toroidal bag 354a, if not already unexpanded, is forcibly brought to an unexpanded state by the convergence in space of the inner cylinder's wall 362 and the first intermediate cylinder's wall 364. Meanwhile, the hinge 316 causes the beak 320 to be redirected once the beak 320 contacts the wall 364 so that the puncturing surface does not face the more proximally located toroidal bags 354 (bags 354b and 354c in FIG. 12A). As a result, the surgeon's continued application of a pulling force on the trip wire 78 does not cause additional bands to fire because the toroidal bags 354b and 354c remain in an expanded or inflated condition and thereby provide a positive stop against proximal motion of either the first or second intermediate cylinders 344, 346, and against dispensing the bands 50b or 50c. However, release of the proximal controller 36 permits the release mechanism 300 to return to its nominal rest position and the beak 320 to re-orient toward the toroidal bags 354 (see FIG. 12) for puncturing another bag upon a subsequent actuation of the proximal controller 36.

Fourth Embodiment

With reference now to FIGS. 13–17, a fourth embodiment of a ligating instrument dispenser constructed in accordance with this invention is illustrated. A dispenser 440 again comprises telescoping cylinders 442, 444, 446 having ligating bands 50 disposed thereon. In FIG. 13, the dispenser 440 is shown assembled onto the tubular housing 32 and in a fully loaded state immediately prior to placement of a ligating band on the tissue 90. The inner cylinder 442 includes a boss 402 having an axially directed aperture 404 therethrough for receiving the trip wire 78A. The trip wire 78A is anchored distal to the boss 402 by an anchor 408. The trip wire 78A extends proximally through, for example, the biopsy channel 76 to the proximal end of the tubular housing 32. A pulling force applied to the trip wire 78A draws the inner cylinder 442 proximally (to the left in the figure) when a pull wire locking mechanism 454 (described below) is released. The trip wire 78A may be rotatably mounted in the aperture 404, although this is not critical to this fourth embodiment.

According to the construction of this embodiment, the pull wire locking mechanism 454 comprises selectively removable spacers interposed axially between each of the cylinders 442, 444, 446, and 448. Cylinders 442, 444, 446, and 448 have proximal walls 462, 464, 466, 468, respectively, which preferably extend radially inwardly, against which are seated the selectively removable spacers. Together, the spacers and the walls 462, 464, 466, 468 of this embodiment comprise a positive stop which precludes the possibility of firing multiple ligation bands 50 with a single actuation of the proximal controller 36. The spacers comprise pull wires 454a, 454b, and 454c which extend from the proximal end of the tubular housing 32 for manipulation by the surgeon to the dispenser 440. Preferably, the pull wires 454 are flattened at their respective distal ends to have a flattened dimension that is approximately the width of a ligating band 50, or greater (see FIG. 13A). In addition, the pull wires are preferably reshaped into an arcuate configuration, for example, into a loop, and bent so that the loop is oriented transverse to the center line of the dispenser 440, that is, so the loop generally traverses the diameter of one of the telescoping cylinders. In the fully loaded state of FIG. 13, the pull wire 454a has been formed into a loop of greater diameter than the inside diameter of the first intermediate cylinder 444 so that the flattened portion of the pull wire precludes proximal motion of the inner cylinder 442 even if a pulling force is applied to the trip wire 78A by the proximal controller 36. Likewise, the pull wire 454b has a distal loop of greater diameter than the inside diameter of the second intermediate cylinder 446 so that the flattened portion of the pull wire precludes proximal motion of the first intermediate cylinder 444 and the pull wire 454c has a distal loop of greater diameter than the inside diameter of the outer cylinder 448 so that the flattened portion of the pull wire precludes proximal motion of the second intermediate cylinder 446.

At the proximal end of the tubular housing 32, the pull wires 454a, 454b, and 454c may be coded (for example, with different colors, labels, or both) so that the surgeon can selectively retract one of pull wires 454a, 454b, and 454c and thereafter apply a pulling force to the trip wire 78A to draw the cylinders proximally and dispense the ligating bands 50, as previously described.

FIGS. 15A, 15B, and 15C illustrate cross sections of various channel 76 configurations that may be provided in the tubular housing 32, or in a multilumen catheter 476 inserted therethrough. Each figure illustrates a lumen 478A for the trip wire 78A and a plurality of lock mechanism lumens for the pull wires 454a, 454b, and 454c. In FIG. 15A, the lock mechanism lumens 480a, 480b, and 480c are respectively adapted to accommodate pull wires 454a, 454b, and 454c, as well as their flattened portions. In FIG. 15B, is a variation in which the lock mechanism lumens 482a, 482b, and 482c are respectively adapted to accommodate pull wires 454a, 454b, and 454c of irregular cross section. FIG. 15C is similar to FIG. 15B, but includes an additional lumen 486 to accommodate an additional pull wire, for example, a pull wire 454d to dispense a fourth ligation band 50d, or for a Seldinger guide wire or other catheter or catheter mounted device.

In FIG. 16, pull wires 454a and 454b have been retracted and tension applied to the trip wire 78A to successively dispense the ligating bands 50a and 50b at distinct locations on the tissue 90 to accomplish ligation thereof. The pull wire 454c has not been retracted and therefore provides a positive stop to the telescoping motion of the cylinders 442 and 444. In particular, the pull wire 454c, being interposed between the outer cylinder 448 and the second intermediate cylinder 446, precludes further telescoping motion of the cylinders 442 and 444, and inadvertent dispensing of the ligating band 50c which remains mounted on the second intermediate cylinder 446.

The embodiment of FIGS. 13-17 need not include the aforementioned slots 56, 60, and 62 and complementary protuberances 58, 64, and 66 to maintain structural integrity and limit the travel of the cylinders 442, 444, 446, and 448. Referring now to FIG. 17, there is seen a friction membrane 488 disposed in the proximal end wall 468 of the outer cylinder 448 in the path of the trip wire 78A. The friction membrane 488 has a round, central bore 490 that is preferably just slightly larger in diameter than the nominal diameter of the trip wire 78A. The bore 490 is surrounded by flaps 492 adapted to deflect in response to the passage of an object through the bore 490 that is slightly larger than the diameter of the bore 490. The trip wire 78A has a ribbed distal segment 494 having a cross section that is formed larger than the nominal diameter of the trip wire's 78A proximal segment, and selected to frictionally passes through the bore 490 by causing the flaps 492 to deflect. By drawing the trip wire 78A through the channel 76 or catheter 476 a distance sufficient to cause the distal ribbed segment 494 to engage the flaps 492, the assembly is secured and there is little risk of the cylinders 442, 444, 446, and 448 separating when the dispenser 440 is used. In combination with the walls 462, 464, 466, and 468 which seat the flattened distal end of the pull wires 454, the proximal travel of any of the sliding cylinders 442, 444, and 446 is limited. The friction membrane 488 may be molded in the outer cylinder 448 to comprise a single element.

Fifth Embodiment

Figure 18:
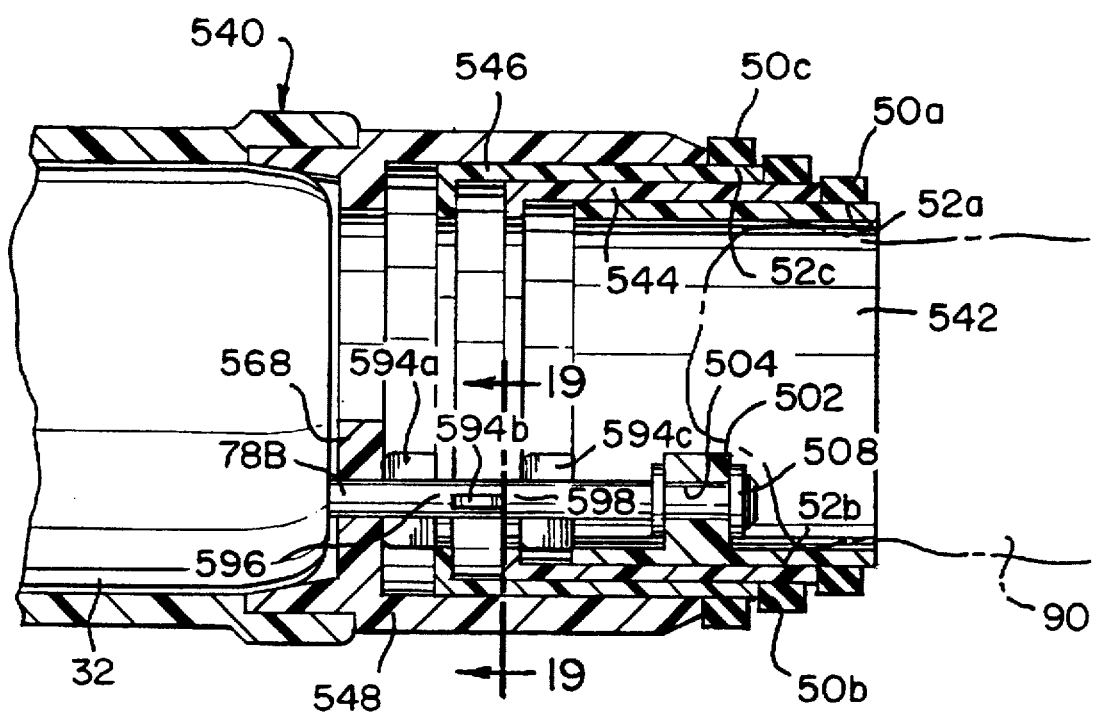
FIG. 18 is a cross sectional view of a fifth embodiment of a ligating instrument dispenser according to this invention, showing the device in assembled form and in a fully loaded state immediately prior to placement of a ligating band, and showing a trip wire.
Figure 19:
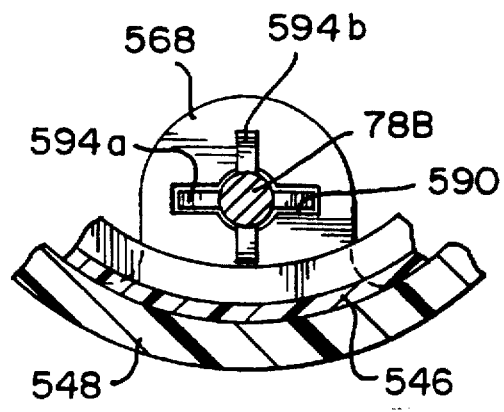
FIG. 19 is a cross sectional view taken along line 19—19 in FIG. 18, with the trip wire shown in a rotated state relative to FIG. 18.

With reference now to FIGS. 18 and 19, a fifth embodiment of a ligating instrument dispenser 540 according to this invention is illustrated. The dispenser 540 includes telescoping cylinders 542, 544, 546 having ligating bands 50 disposed thereon. In FIG. 18, the dispenser 540 is shown assembled onto the tubular housing 32 and in a fully loaded state. The inner cylinder 542 includes a boss 502 having an axially directed aperture 504 therethrough (see FIG. 19) for receiving a keyed trip wire 78B. The trip wire 78B is anchored on the distal side of the boss 502 by an anchor 508 which may be a separate element attached to the trip wire 78B, or a deformed or reshaped portion of the trip wire 78B itself. The trip wire is mounted for axial rotation independent of the inner cylinder 542 in the aperture 404; however, the trip wire 78B is axially fixed with respect to the inner cylinder 542 by the anchor 508 so that a pulling force on the trip wire 78B causes the cylinders to telescope and thereby dispense a ligating band 50. The trip wire 78B extends proximally through, for example, a biopsy channel 76 to the proximal end of the tubular housing 32, and has a keyed distal portion comprising flared segments 594a, 594b, and 594c that are adapted to preclude inadvertent or premature dispensing of a ligating band 50, as described next. The flared segments 594a, 594b, and 594c are separated by wire segments 596, 598 of substantially the same cross section as the proximal segment of the trip wire 78B.

According to the construction of this embodiment, the outer cylinder 548 includes a boss or mounting stop 568 having a keyed aperture 590 formed therein (see FIG. 19) for receiving the keyed trip wire 78B and for conveying actuation forces to the telescoping cylinders 542, 544, 546 so that the ligating bands 50a, 50b, and 50c can be dispensed. In combination with the flared segments 594a, 594b, and 594c, the keyed aperture 590 comprises the positive stop mechanism of this embodiment. The flared segments 594a, 594b, and 594c may comprise a series of rotationally displaced, keyed or otherwise formed wire segments. In FIG. 18, the flared segment 594a is keyed in a generally vertical direction, the next flared segment 594b is keyed in a generally horizontal direction, that is, approximately 90° offset from segment 594a, and the flared segment 594c is keyed in a generally vertical direction, also approximately 90° offset from the previous segment, segment 594b. The keyed aperture 590 can be of any non-circular shape that complements the formations on the trip wire 78B to provide the aforementioned positive stop mechanism, for example, sinusoidal, trapezoidal, rectangular, and so on. All that is required is that the keyed aperture 590 be formed in a manner sufficient to prevent premature firing of any of the ligating bands 50, that is, be formed to restrain axial movement of the trip wire 78B unless the flared segment 594 just distal to the keyed aperture 590 is first rotated into alignment with the keyed aperture 590. Along this line of reasoning, note that the positive stop mechanism is achievable with a wide variety of keyed or otherwise formed wire segments 594, and by other modifications to the trip wire 78B such as by attaching elements that selectively pass through the keyed aperture 590 when suitably rotationally aligned, as by soldering, welding, brazing, adhering, and the like, and by flattening or deforming the flared wire segments. In each of these forms, the positive stop mechanism results whenever the keyed segments are serially positioned with differing rotational orientations, as shown in FIG. 18.

In operation, the surgeon manipulates a proximal controller 36 to rotate the keyed trip wire 78B until the segment 594a is aligned with the keyed aperture 590, as shown in FIG. 19. Once so aligned, the trip wire 78B can be pulled to draw the inner cylinder 542 proximally. The dispenser 540 is designed to first dispense the least stretched ligating band, band 50a, as the other bands are stretched around larger diameter cylinders and thereby require progressively greater displacement forces to dispense them, as previously described. The dispenser 540 may be adapted to preferentially favor the firing of one band before another using coatings or varied surface configurations to reduce the relative frictional forces that otherwise oppose the dispensing of a particular band 50.

With the trip wire 78B aligned as shown in FIGS. 18 and 19, it is pulled proximally to dispense the ligating band 50a. The trip wire 78B tows the inner cylinder 542 proximally until the segment 594b abuts the keyed aperture 590, as shown in FIG. 19. At this stage, the dispenser 540 is in a partially loaded state (substantially as shown in FIG. 8 with respect to the relative location of the cylinders and bands only), with the inner cylinder 542 fully telescoped into the first intermediate cylinder 544, and the ligating bands 50b and 50c loaded on the first and second intermediate cylinders 544, 546, respectively. Because the segment 594b has its keyed portion rotationally offset from that of segment 594a, the segment 594b cannot pass through the keyed aperture 590, and continued pulling on the trip wire 78B does not permit additional ligating bands to be dispensed. The dispenser 540 and tubular housing 32 may now be repositioned within the patient and the segment 596 of the trip wire 78B rotated in the keyed aperture 590 until the distal segment 594b is aligned therewith. When the segment 594b is so aligned with the keyed aperture 590 (not shown), the ligating band 50b can be dispensed (as that is typically the band with the next lowest frictional force opposing its displacement) by pulling on the trip wire 78B. Now, the dispenser 540 has the inner cylinder 542 fully telescoped into the first intermediate cylinder 544, and the first intermediate cylinder 544 fully telescoped into the second intermediate cylinder 546, and only the second intermediate cylinder 546 has a ligating band 50c loaded on it to be dispensed (compare to FIG. 15). The trip wire 78B is now positioned with the segment 594c abutting the keyed aperture 590 and is not able to pass therethrough until after the segment 598 of the trip wire 78B is rotated to align the flared segment 594c. Finally, the dispenser 540 and tubular housing 32 may be again repositioned within the patient, and the trip wire 78B can dispense the only remaining ligating band, band 50c, by pulling the aligned trip wire 78B.

Conclusion

In summary, several embodiments of a multifiring ligating band dispenser apparatus that may be mounted on a conventional endoscope or other catheter are disclosed. Each embodiment provides a positive stop mechanism to ensure that only one band fires with a single actuation of the proximal controller 36.

The cylinders 42, 44, 46 (and cylinders 242, 244, 246, 342, 344, 346, 442, 444, 446, 542, 544, and 546, the "sliding cylinders") and cylinder 48 (and cylinders 248, 348, 448, and 548, the "outer cylinders") are preferably formed of substantially transparent polycarbonate. When each of the sliding and outer cylinders is made of a substantially transparent plastic material, a wide field of view is afforded when the ligating instrument 30 or endoscope includes conventional viewing optics. Alternatively, the sliding and outer cylinders may be made of steel or other comparatively high strength, rigid material so that each cylinder can have a small wall thickness yet retain sufficient rigidity to resist collapsing under the hoop stress caused by the ligating bands 50 stretched thereover. The use of stainless steel cylinders, or other relatively stiff, high strength thin material, allows multiple cylinders to be incorporated into the dispenser structure so that additional bands 50, for example, five bands, can be dispensed without reloading or withdrawal of the instrument 30 from the patient. In its fully loaded state, some "tunnel vision" is to be expected due to a restriction of the field of view because the dispenser 40 (and dispensers 240, 340, 440, and 540) and the bands 50 extend beyond the distal end face 72 of tubular housing 32, or beyond the end of the conventional endoscope, and thus beyond the viewing optics. A dispensing apparatus may readily be modified, however, so that the viewing optics extends at least partially distally through the telescoping cylinders, thus reducing this effect.

Other structures for providing the definite, telescoping motion of the sliding cylinders could be substituted for the disclosed mechanism. In addition, the lock mechanisms (54, 254, 354, 454, and 554) of the various embodiments can readily be interchanged for one another, or for an equivalent mechanism that prevents inadvertent firing of a ligating band by restraining axial motion of the cylinders.

The embodiments shown in FIGS. 1 through 19 disclose a ligating band dispenser for a ligating instrument. The dispenser can dispense a single ligating band at a given location, or multiple ligating bands at a single location, or one or more bands at different locations. The surgeon may perform multiple ligating operations at different locations without having to withdraw the ligating instrument after each ligating band is dispensed. In general, the number of bands B that can be dispensed, provided one band is disposed on each cylinder C, is C-1. The cylinders can be configured to accommodate additional bands by increasing one or more of the cylinder's axial length and adjusting size of the slot 56, 58, 60 for that cylinder so that the additional axial travel that would be required can be accommodated.

The cylinders that support the ligating bands 50 need not be cylindrical. Support members of varying cross-sections may be provided, for example, square, rectangular, triangular, etc. Thus, a first support member may replace the inner cylinder, a second support member may replace the intermediate cylinder(s), and a fixed member may replace the outer cylinder.

The foregoing embodiments have been described with respect to certain presently preferred dimensions that provide a dispenser that is suitable for deploying ligating bands 50 on any soft tissue in conjunction with an endoscope, for example, varices in the fundal region or stomach lining, or certain sized varices or internal hemorrhoids. However, other dimensions may be more particularly suitable for ligating a particular varix, internal hemorrhoid, or internal body structure or duct, as the case may be. Accordingly, the present invention is not limited in its utility to the foregoing dimensions.

Although this structure has been shown with respect to a particular ligating instrument 30, it will be apparent that dispensers 40, 240, 340, 440, and 540 constructed in accordance the disclosed embodiments are readily adapted for connection with a wide variety of structures including those based upon rigid or flexible endoscopic structures, as previously mentioned herein. It will also be apparent that these dispensers are reliable, readily producible, and structurally sound. The use of the disclosed trailing links and keyed apertures prevents premature dispensing of the ligating bands so that the requirement for the use of over tubes or separate stoppers is not required with ligating instruments incorporating this invention.

The ligating instrument is simple to use because it is merely necessary for the surgeon to position the ligating instrument and then actuate the trip wire 78. There is no need for the surgeon to sense the amount of travel required for depositing a single ligating band or a single set of ligating bands.

While this invention has been disclosed in terms of a particular embodiment and certain modifications, it will be apparent that many other modifications can be made to the specifically disclosed apparatus without departing from the invention. Therefore, it is the intent of the appended claims to cover all such variations and modifications as come within the true spirit and scope of this invention.

What is claimed is:

1. A ligating band dispenser for dispensing a plurality of elastic ligating bands onto at least one internal tissue site within a patient's body, comprising:

an inner cylinder having proximal and distal portions, the inner cylinder being adapted to support at least one ligating band in a stretched condition about the distal portion thereof;

an intermediate cylinder having proximal and distal portions and a distal end, the intermediate cylinder being positioned about at least the proximal portion of the inner cylinder and adapted to support at least another ligating band in a stretched condition about the distal portion thereof, the inner and intermediate cylinders comprising axially sliding cylinders;

an outer cylinder positioned about at least the proximal portion of the intermediate cylinder, the outer cylinder having a distal end, the sliding cylinders being axially slidably mounted with respect to the outer cylinder;

a trip wire connected to the inner cylinder and extending proximally therefrom, the trip wire being adapted to cause an axially sliding motion of the sliding cylinders during an application of force to the trip wire;

restraining means associated with each sliding cylinder for restraining sliding motion thereof during the application of force to the trip wire; and releasing means for releasing the restraining means associated with one of the sliding cylinders upon the application of the pulling force, whereby the released sliding cylinder slides and the distal end of one of the intermediate and outer cylinders pushes the ligating band therefrom during the application of the pulling force.

2. The dispenser as in claim 1, wherein the intermediate cylinder comprises first and second intermediate cylinders, one of which is positioned about the proximal portion of the other, and wherein each of the first and second intermediate cylinders is respectively adapted to support a different one of the ligating bands in a stretched condition about the distal portion thereof.

3. The dispenser as in claim 1, wherein the restraining means comprises one of an axially directed spring tab and a circumferentially directed spring tab.

4. The dispenser as in claim 1, wherein the restraining means comprises a plurality of spacers, the spacers being separately, removably disposed proximate to each sliding cylinder.

5. The dispenser as in claim 1, wherein the restraining means comprises an expanded toroidal bag.

6. The dispenser as in claim 5, wherein the releasing means comprises:

a pivot coupled to the inner cylinder;

an arm coupled to the pivot and positionable to engage the expanded toroidal bag upon the application of the pulling force, the arm including a surface adapted to puncture the expanded toroidal bag when positioned in contact therewith.

7. The dispenser as in claim 6, wherein the arm is hingedly coupled to the pivot for rotation relative to the pivot.

8. The dispenser as in claim 7, wherein the arm is adapted to engage the expanded toroidal bag upon the application of the pulling force and rotate toward the pivot with the sliding of the inner cylinder.

9. The dispenser as in claim 1, wherein the restraining means comprises:

a keyed aperture fixedly positioned with respect to the sliding cylinders; and a keyed distal segment on the trip wire.

10. The dispenser as in claim 9, wherein the keyed distal segment comprises a plurality of rotationally offset elements.

11. The dispenser as in claim 10, wherein the rotationally offset elements are one of deformed in or attached to the trip wire.

12. The dispenser as in claim 10, wherein the trip wire is mounted for axial rotation in the inner cylinder, whereby the keyed distal segment is rotated with respect to the keyed aperture until aligned.

13. The dispenser as in claim 1, wherein the releasing means comprises:

a pivot having an arm, the pivot being pivotally coupled to the inner cylinder.

14. The dispenser as in claim 13, wherein the pivotal coupling of the pivot is by one of a pivot pin and a living hinge.

15. The dispenser as in claim 14, wherein the pivotal coupling includes biasing means to maintain the arm in a position clear of the restraining means except when the pulling force is being applied to the trip wire.

16. The dispenser as in claim 13, wherein the arm is positionable with respect to the inner cylinder to engage the restraining means associated with one of the sliding cylinders upon the application of the pulling force.

17. The dispenser as in claim 13, wherein the arm is hingedly coupled to the pivot.

18. The dispenser as in claim 17, wherein the hinged coupling of the arm is by one of a pivot pin and a living hinge.

19. The dispenser as in claim 18, wherein the hinged coupling includes biasing means to maintain the arm in a position to engage the restraining means upon application of the pulling force to the trip wire, the force applied by the biasing means being overcome during the sliding of the inner cylinder by the frictional forces of the engagement of the arm and the release mechanism, whereby the engaged arm hinges toward the pivot with the sliding of the inner cylinder.

20. The dispenser as in claim 1, further comprising a hollow tubular housing, wherein the dispenser is mounted at the distal end thereof.

21. The dispenser as in claim 20, wherein the hollow tubular housing is one of a flexible endoscope and a rigid introducer.

22. The dispenser as in claim 20, further comprising:

means secured to the trip wire and positioned at the proximal end of the tubular housing for moving the trip wire proximally to cause dispensing of a ligating band.

23. The dispenser as in claim 20, further comprising:

means for drawing an internal tissue site within the distal portion of the inner cylinder.

24. The dispenser as in claim 1, further comprising:

a tubular housing having a proximal handle end, a distal end, and a lumen therebetween, the outer cylinder being fixedly coupled to the distal end of the housing.

25. The dispenser as in claim 24, wherein the trip wire is connected at a proximal end thereof to the proximal handle end.

26. The dispenser as in claim 1, wherein the dispenser is made of one of stainless steel and polycarbonate.

27. The dispenser as in claim 1, wherein the sliding cylinders are mounted for telescoping movement.

28. The dispenser as in claim 27, wherein adjacent telescoping sliding cylinders have inside and outside diameters chosen to have an annular gap therebetween that is insufficient to permit the ligating bands to become crimped when the sliding cylinders slide.

29. The dispenser as in claim 1, wherein the sliding cylinders are coaxially mounted.

30. The dispenser as in claim 1, wherein the intermediate cylinder is positioned in surrounding relation to at least the proximal portion of the inner cylinder and the outer cylinder is positioned in surrounding relation to at least the proximal portion of the intermediate cylinder.

31. The dispenser as in claim 1, wherein the intermediate cylinder comprises a succession of intermediate cylinders, each of which is positioned about the proximal portion of a preceding cylinder and has at least a further ligating band thereabout, the succession of cylinders being arranged so that they telescope sequentially with successive applications of pulling forces on the pull wire to push the ligating bands from one of the preceding and inner cylinders.

32. The dispenser as in claim 1, wherein the releasing means releases the restraining means associated with another of the sliding cylinders upon a successive application of the pulling force.

33. The dispenser as in claim 1, further comprising complementary apertures and protuberances formed on adjacent ones of the inner, intermediate, and outer cylinders, the apertures having predetermined lengths, the protuberances of one cylinder being received in the slots of an adjacent cylinder, whereby the travel of the sliding cylinders is defined by the predetermined lengths of the apertures.

34. A ligating band dispenser for dispensing a plurality of elastic ligating bands onto at least one internal tissue site within a patient's body, comprising:
   a first support member having proximal and distal portions, the first support member being adapted to support at least one ligating band in a stretched condition about the distal portion thereof;
   a second support member having proximal and distal portions and a distal end, the second support member being positioned about at least the proximal portion of the first support member and adapted to support at least another ligating band in a stretched condition about the distal portion thereof, the first and second support members comprising axially sliding support members;
   a fixed member positioned about at least the proximal portion of the second support member, the fixed member having a distal end, the sliding support members being axially slidably mounted with respect to the fixed member;
   a trip wire connected to the first support member and extending proximally therefrom, the trip wire being adapted to cause an axially sliding motion of the sliding support members when pulled, whereby the distal end of one of the second support and fixed members pushes the ligating band therefrom;
   restraining means associated with each sliding support member for restraining sliding motion thereof during the application of force to the trip wire; and
   releasing means for releasing the restraining means associated with one of the sliding support members upon the application of the pulling force.

35. The dispenser as in claim 34, wherein the first and second support members and the fixed member are generally hollow.

36. The dispenser as in claim 34, wherein the second support member comprises a succession of intermediate support members, each of which is positioned about the proximal portion of a preceding support member and has at least a further ligating band thereabout, the succession of support members being arranged so that they telescope sequentially with successive applications of pulling forces on the pull wire to push the ligating bands from one of the preceding and first support members.

37. The dispenser as in claim 34, wherein the releasing means releases the restraining means associated with another of the sliding support members upon a successive application of the pulling force.

38. The dispenser as in claim 34, further comprising complementary apertures and protuberances formed on adjacent ones of the sliding support members and the fixed member, the apertures having predetermined lengths, the protuberances of one support member being received in the slots of an adjacent support member, whereby the travel of the sliding support members is defined by the predetermined lengths of the apertures.

39. The dispenser as in claim 34, wherein the restraining means comprises one of an axially directed spring tab and a circumferentially directed spring tab.

40. The dispenser as in claim 34, wherein the restraining means comprises:
   a keyed aperture fixedly positioned with respect to the sliding support members; and
   a keyed distal segment on the trip wire.

41. The dispenser as in claim 40, wherein the keyed distal segment comprises a plurality of rotationally offset elements.

42. The dispenser as in claim 41, wherein the rotationally offset elements are one of deformed in or attached to the trip wire.

43. The dispenser as in claim 41, wherein the trip wire is mounted for axial rotation in the first support member, whereby the keyed distal segment is rotated with respect to the keyed aperture until aligned.

44. The dispenser as in claim 34, wherein the releasing means comprises:
   a pivot having an arm, the pivot being pivotally coupled to the first support member.

45. The dispenser as in claim 44, wherein the pivotal coupling includes biasing means to maintain the arm in a position clear of the restraining means except when the pulling force is being applied to the trip wire.

46. The dispenser as in claim 44, wherein the arm is positionable with respect to the first support member to engage the restraining means associated with one of the sliding support members upon the application of the pulling force.

47. The dispenser as in claim 44, wherein the arm is hingedly coupled to the pivot.

48. The dispenser as in claim 47, wherein the hinged coupling includes biasing means to maintain the arm in a position to engage the restraining means upon application of the pulling force to the trip wire, the force applied by the biasing means being overcome during the sliding of the first support member by the frictional forces of the engagement of the arm and the release mechanism, whereby the engaged arm hinges toward the pivot with the sliding of the first support member.

49. The dispenser as in claim 34, further comprising:
   a tubular housing having a proximal handle end, a distal end, and a lumen therebetween, the fixed member being fixedly coupled to the distal end of the housing, the trip wire extending proximally through the lumen.

50. The dispenser as in claim 34, wherein adjacent sliding support members have inside and outside dimensions chosen to have a gap therebetween that is insufficient to permit the ligating bands to become crimped when the sliding support members slide.

51. The dispenser as in claim 34, wherein the second support member is positioned in surrounding relation to at least the proximal portion of the first support member and the fixed member is positioned in surrounding relation to at least the proximal portion of the first support member.

* * * * *